| (12) | United States Patent | (10) Patent No.: US 10,024,858 B2 |
|---|---|---|
| | Smith et al. | (45) Date of Patent: Jul. 17, 2018 |

(54) PORTABLE BLOOD COUNT MONITOR

(71) Applicants: Tahoe Institute for Rural Health Research, LLC, Truckee, CA (US); The Regents of The University of California, Oakland, CA (US)

(72) Inventors: Zachary Smith, Sacramento, CA (US); Tingjuan Gao, Elk Grove, CA (US); Stephen Lane, Oakland, CA (US); Sebastian Wachmann-Hogiu, Sacramento, CA (US); Denis Dwyre, Davis, CA (US); Laurence Heifetz, Truckee, CA (US); James Hood, Truckee, CA (US); Dennis Matthews, Truckee, CA (US); Keith Tatsukawa, Truckee, CA (US)

(73) Assignees: TAHOE INSTITUTE FOR RURAL HEALTH, LLC, Truckee, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/207,274

(22) Filed: Mar. 12, 2014

(65) Prior Publication Data

US 2014/0273064 A1 Sep. 18, 2014

Related U.S. Application Data

(60) Provisional application No. 61/890,071, filed on Oct. 11, 2013, provisional application No. 61/878,431, (Continued)

(51) Int. Cl.
*G01N 31/22* (2006.01)
*G01N 33/574* (2006.01)
*G01N 33/50* (2006.01)

(52) U.S. Cl.
CPC ... *G01N 33/57438* (2013.01); *G01N 33/5017* (2013.01)

(58) Field of Classification Search
CPC ... G01N 2015/0065; G01N 2015/0084; G01N 2015/008; G01N 33/5094; G01N 15/1429;
(Continued)

(56) References Cited

U.S. PATENT DOCUMENTS

| 4,654,197 A | * | 3/1987 | Lilja | ............... B01L 3/5027 204/403.02 |
|---|---|---|---|---|
| 6,350,613 B1 | | 2/2002 | Wardlaw et al. | |

(Continued)

FOREIGN PATENT DOCUMENTS

| WO | WO 99/52633 A1 | 10/1999 |
|---|---|---|
| WO | WO-2014159692 A1 | 10/2014 |

OTHER PUBLICATIONS

HemoCue Webpage Mar. 11, 2013. http://www.hemocue.com/international/Products/White_Blood_Cell_count-1170.html.
(Continued)

*Primary Examiner* — Dennis White
(74) *Attorney, Agent, or Firm* — Wilson Sonsini Goodrich & Rosati

(57) ABSTRACT

This disclosure describes the development of a sample preparation, measurement, and analysis method that permits accurate characterization of red blood cells, platelets, and white blood cells, including a 3-part differential of the white blood cells count, to be performed on small volumes of a biological sample. This method is compatible with compact and portable instrumentation that permits the sample collection to be performed in a subject's home and analysis to be performed elsewhere by transmission of the data to a laboratory or doctor's office.

63 Claims, 14 Drawing Sheets

Related U.S. Application Data filed on Sep. 16, 2013, provisional application No. 61/780,732, filed on Mar. 13, 2013.

(58) Field of Classification Search
CPC ..... G01N 2015/1493; G01N 33/56972; G01N 2021/058; B01L 2200/0652; B01L 9/527
See application file for complete search history.

(56) References Cited

U.S. PATENT DOCUMENTS

| | | |
|---|---|---|
| 6,469,311 B1 | 10/2002 | Modlin et al. |
| 6,537,501 B1 | 3/2003 | Holl et al. |
| 6,831,735 B2 | 12/2004 | Tsukada |
| 6,869,798 B2 | 3/2005 | Crews et al. |
| 6,959,618 B1 | 11/2005 | Larsen |
| 7,413,905 B2 | 8/2008 | Xu et al. |
| 7,493,219 B1 | 2/2009 | Qi et al. |
| 7,592,179 B2 | 9/2009 | Guo |
| 7,617,743 B2 | 11/2009 | Zhang et al. |
| 7,630,063 B2 | 12/2009 | Padmanabhan et al. |
| 7,659,122 B2 | 2/2010 | Guo |
| 7,701,193 B2 | 4/2010 | Petersen et al. |
| 7,738,094 B2 | 6/2010 | Goldberg |
| 7,771,658 B2 | 8/2010 | Larsen |
| 7,797,990 B2 | 9/2010 | Larsen et al. |
| 8,071,051 B2 | 12/2011 | Padmanabhan et al. |
| 8,224,058 B2 | 7/2012 | Lindberg et al. |
| 8,247,191 B2 | 8/2012 | Ritzen et al. |
| 2001/0028862 A1 | 10/2001 | Iwata et al. |
| 2003/0027225 A1 | 2/2003 | Wada et al. |
| 2003/0133840 A1 | 7/2003 | Coombs et al. |
| 2005/0255001 A1* | 11/2005 | Padmanabhan .... G01N 15/1404 422/73 |
| 2006/0195047 A1* | 8/2006 | Freeman ............. A61B 5/1411 600/583 |
| 2006/0211071 A1 | 9/2006 | Andre et al. |
| 2006/0257993 A1* | 11/2006 | McDevitt .......... B01L 3/502715 435/287.2 |
| 2007/0077550 A1 | 4/2007 | Tohma et al. |
| 2007/0172388 A1* | 7/2007 | Padmanabhan et al. ....... 422/58 |
| 2008/0025872 A1 | 1/2008 | Dykes et al. |
| 2009/0191583 A1 | 7/2009 | Fernandez-Salas et al. |
| 2009/0215072 A1 | 8/2009 | McDevitt et al. |
| 2010/0093105 A1* | 4/2010 | Lee ....................... B07C 5/3416 436/171 |
| 2011/0104009 A1 | 5/2011 | Kawamura et al. |
| 2012/0176498 A1 | 7/2012 | Haas et al. |
| 2014/0270458 A1 | 9/2014 | Smith et al. |

OTHER PUBLICATIONS

International search report and written opinion dated Jun. 17, 2014 for PCT/US2014/024777.

Office action dated Nov. 6, 2015 for U.S. Appl. No. 14/207,300.

Gao, et al. Smart and Fast Blood Counting of Trace Volumes of Body Fluids from Various Mammalian Species Using a Compact, Custom-Built Microscope Cytometer. Anal Chem. Dec. 1, 2015;87(23):11854-62. doi: 10.1021/acs.analchem.5b03384. Epub Nov. 10, 2015.

Invitrogen. Countless Automated Cell Counter. User Manual. Catalog No. C10227. Rev. Date Sep. 15, 2009. MP10227. 39 pages.

Office Action dated Oct. 25, 2016 for U.S. Appl. No. 14/207,300.

Smith, et al. Single-step preparation and image-based counting of minute volumes of human blood. Lab Chip. Aug. 21, 2014;14(16):3029-36. doi: 10.1039/c4lc00567h. Epub Jun. 23, 2014.

Smith, et al. Smart and Fast Blood Counting of Trace Volumes of Body Fluids from Various Mammalian Species Using a Compact, Custom-Built Microscope Cytometer. Conference Presentation. Abstract. Proc. of SPIE. 2016. vol. 9715. 97150J-Z. 1 page.

Office Action dated May 10, 2017 for U.S. Appl. No. 14/207,300.

European search report with written opinion dated Dec. 7, 2016 for EP Application No. 14774289.

Office Action dated Dec. 4, 2017 for U.S. Appl. No. 14/207,300.

\* cited by examiner

Panel A

Panel B

Panel A

Panel B

Panel C

PORTABLE BLOOD COUNT MONITOR

CROSS-REFERENCE

This application claims the benefit of U.S. Provisional Application No. 61/890,071, filed on Oct. 11, 2013; U.S. Provisional Application No. 61/878,431, filed on Sep. 16, 2013; and U.S. Provisional Application No. 61/780,732, filed on Mar. 13, 2013, the contents of each of which is incorporated herein by reference in its entirety.

STATEMENT AS TO FEDERALLY SPONSORED RESEARCH

This invention was made with partial government support under an Acceleration of Innovation Research grant awarded by the National Science Foundation (NSF Accelerating Innovation Research Grant No. 1127888, entitled "Creation of an Ecosystem for Biophotonic Innovation" and dated Aug. 1, 2011 to Jul. 31, 2013), as well as from the Center for Biophotonics Science and Technology, a designated NSF Science and Technology Center managed by the University of California, Davis, under Cooperative Agreement No. PHY0120999. The government has certain rights in the invention.

BACKGROUND

Home or personal testing can minimize the need for monitoring tests to be performed at clinics or laboratories, reduce the costs of healthcare, and improve the quality of life of a subject. Testing remains a critical aspect of the quality of life for many people, especially the elderly and infirmed, who may be unable or unwilling to travel to obtain the appropriate monitoring services to sustain their health. Home testing is frustrated by the complexity of medical instruments, difficulty of use, cost, and unavailability to the general public. Several challenges exist in creating and providing systems, devices, and methods that can offer laboratory quality testing outside of a laboratory.

SUMMARY OF THE INVENTION

In some embodiments, the invention provides a device comprising: a) a slide configured to receive a body fluid, wherein the slide comprises: i) a first chamber, wherein the first chamber contains a first reagent capable of detecting a first analyte in the body fluid; and ii) a second chamber, wherein the second chamber contains a second reagent capable of detecting a second analyte in the body fluid; and b) an imaging system configured to acquire visual data from the slide.

In some embodiments, the invention provides a device comprising: a) a slide configured to receive a body fluid; b) an imaging system configured to acquire visual data from the slide; and c) a transmitter, wherein the transmitter wirelessly-transmits the acquired visual data over a distance of at least one mile.

In some embodiments, the invention provides a method for analyzing a body fluid, the method comprising: a) providing the body fluid to a slide, wherein the slide comprises a first chamber and a second chamber; b) detecting in the first chamber a first analyte in the body fluid with a first reagent; c) detecting in the second chamber a second analyte in the body fluid with a second reagent; d) acquiring by an imaging system visual data from the slide; e) converting the visual data into at least one image, wherein the converting is performed by a computer system comprising a processor; and f) enumerating, by the processor, at least one analyte in the image.

In some embodiments, the invention provides a system comprising: a) a device comprising: i) a slide configured to receive a body fluid; ii) an imaging system configured to acquire visual data from the slide; and iii) a transmitter, wherein the transmitter wirelessly transmits the acquired visual data; and b) a receiver that receives the wirelessly-transmitted visual data from the transmitter, wherein the transmitter and the receiver are configured to communicate over a distance of at least 1 mile.

In some embodiments, the invention provides a kit comprising: a) a device comprising: i) a slide configured to receive a body fluid, wherein the slide comprises a first chamber and a second chamber; and ii) an imaging system configured to acquire visual data from the slide; b) a first reagent capable of detecting a first cell type in the body fluid; and c) a second reagent capable of detecting a second cell type in the body fluid.

DETAILED DESCRIPTION

Figure 1:
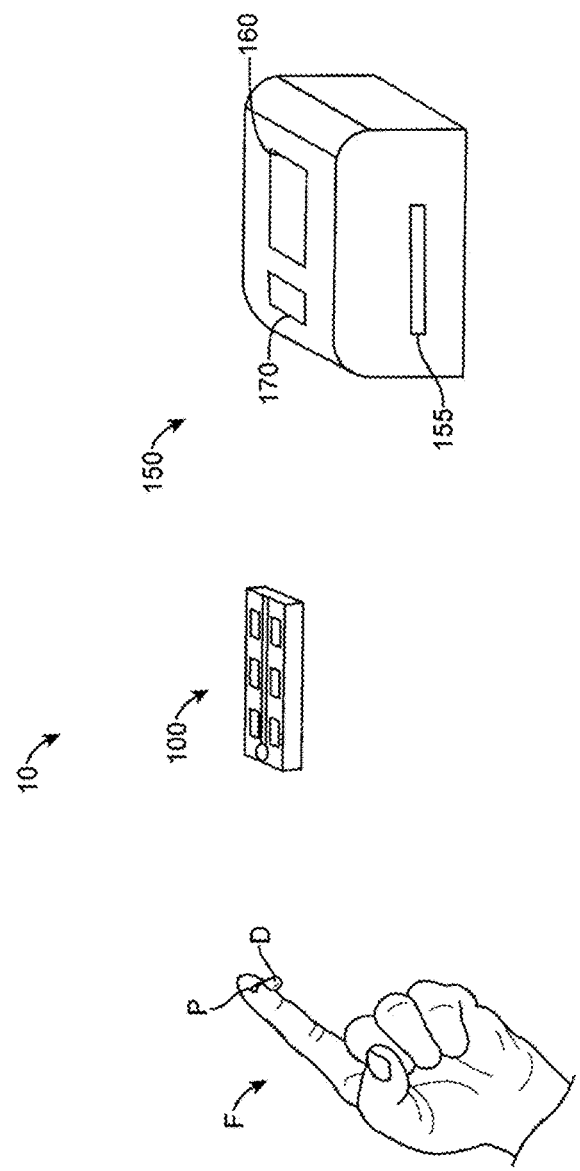
FIG. 1 illustrates a system for analyzing a body fluid.

A complete blood count (CBC) is one of the most common laboratory tests, and blood cell counts can be an important first indicator of disease for many illnesses. A CBC provides information about the cellular portion of the blood—erythrocytes (red blood cells (RBC)), leukocytes (white blood cells (WBC)), and platelets. Abnormally high or low counts of certain cell types can indicate the presence of many forms of disease. Hence, blood counts are among the most commonly performed tests in medicine, as they can provide an overview of a subject's health status as well as response to therapies.

Obtaining a complete blood count ordinarily requires a visit to a clinic, where blood is drawn and analyzed. This practice imposes an inconvenience upon the patient, particularly if the patient is elderly, incapacitated, or resides in a remote area where clinical services are not readily available. For example, a patient living in a rural area might need to travel an excessive distance to obtain a routine assay on a regular basis. This inconvenience not only dissatisfies the patient, but creates the risk of frustrating patient compliance. Moving blood count instrumentation into the home is a challenging way to solve the problem, because the instruments tend to be large and cumbersome, costly, and unintuitive to a person without clinical experience.

CBC data can include not only information about the number of the three cell types, but also information about size and shape of populations and sub-populations of red blood cells and white blood cells. The CBC allows a clinician to have important information about the patient. CBC data, by itself or supplemented with clinical and other laboratory data, can be critical in constructing a differential diagnosis for a patient. Diagnosis is possible by obtaining blood count information and comparing a result to a reference, a standard, or a result obtained with healthy tissue. Specifically, the CBC can give the clinician information about low RBC (anemia), high RBC (erythrocytosis), low WBC (leukopenia), high WBC (leukocytosis), low platelets (thrombocytopenia), high platelets (thrombocytosis), as well as data on low and high counts of the different leukocyte types. The CBC can therefore be an important starting point in forming a clinical diagnosis, screening for changes in patient health, and for monitoring of disease progression or treatment. Currently, CBC is most often performed through a visit to a clinic. A phlebotomist collects a blood sample by drawing blood into a test tube that typically contains an anticoagulant to prevent the collected blood from clotting. The blood sample is then transported to a laboratory for analysis. Alternatively, the blood sample can be drawn off using a "finger-prick," such as the finger-pricks commonly used in diabetes testing. Analysis of the blood sample can be performed manually or in an automated analyzer.

Currently, most blood samples are analyzed automatically by an automated hematology analyzer. For such automatic analysis, a blood sample is first well mixed, usually with an anti-coagulant, and placed on a rack in an analyzer. These analyzers take a few hundred microliters of the prepared blood and combine them with several reagents in a fluidic system. The prepared cells are then passed through one or more laser beams and often through a small, charged aperture. Using a combination of fluorescence signals, light scattering signals, and impedance changes (the Coulter effect), the analyzers detect and enumerate platelets, red cells, and white cells. They analyze the size of red blood cells and determine cellular hemoglobin concentrations. Such analyzers further differentiate subpopulations of white cells (Neutrophils, Lymphocytes, Monocytes, Eosinophils, and Basophils for a 5-part differential count). These analyzers provide fast and accurate measures of blood parameters; however, these instruments require special (often proprietary) reagents, and contain delicate photomultiplier tubes and flow channels. Automated hematology analyzers are bulky, expensive, and technically complex, and all of those factors limit the accessibility and convenience of using automated hematology analyzers. In addition, certain abnormal cells in the blood are usually not identified correctly by an automated analyzer. In those instances, a manual review of a visual field of the sample is required for the identification of any abnormal cells the instrument could not categorize.

Alternative methods for providing a complete blood cell count can rely on manual counting of a sample, for example, on a hemacytometer. Manual CBC is typically performed by viewing a slide prepared with a sample of a subject's blood (a blood film or a peripheral smear) under a microscope. Counting chambers that hold a specified volume of diluted blood (as there are far too many cells if it is not diluted) can be used to calculate the number of red and white cells per liter or microliter of blood. To identify the numbers of different white blood cells, a blood film can be made, and a large number of white blood cells, for example at least 100, can be counted. This count gives a percentage of white blood cells that are of a particular type, for example, granulocytes and monocytes. By multiplying the percentage with the total number of white blood cells, the absolute number of each type of white cell can be obtained. Manual counting methods are often laboriously performed by hand, with technicians manually examining stained cells under a microscope. Hence, manual counting of blood cells in a sample increases the error rate and the cost of the analysis.

Obtaining a blood cell count test in a timely manner is crucial for many subjects undergoing treatment or monitoring their health. For example, most chemotherapy drugs are typically administered every 21 days and can cause myelosuppression, a suppression of the red-blood cells, white blood cells, and platelets. Myelosuppression usually follows a 21 day cyclical fall and recovery in a subject's circulating blood cells. White blood cells and platelets live for about 10 days in circulation while red blood cells live for about 120 days. About 10 days after circulation, the number of white blood cells and platelets are usually at their lowest point or "nadir." If the nadir is too low and the patient has a fever at that time, the patient is regarded as having "febrile neutropenia" and will typically require aggressive intravenous (IV) antibiotics, usually administered during an inpatient setting. While monitoring of the red-blood cell, white blood cell, and platelet count in a subject receiving such a myelosuppressive drug is critical, it can be difficult for the subject to visit a clinic on a regular basis to provide a blood sample. The invention herein satisfies a great need for the development of systems, devices, and methods that can provide an accurate, cost-effective, and efficient blood cell count from a body fluid of a subject that is conveniently achieved.

Described herein are systems, devices, and methods disclosing the development of a method for sample preparation, measurement, and analysis that permits accurate analysis of a body fluid. In some embodiments, the invention provides a novel and simple method for counting red cells, platelets, and white cell subpopulations by using: (i) sub-microliter volumes of blood, (ii) a single-step reagent, and (iii) large-field-of-view, low-magnification imaging. The invention minimizes the number of steps required for sample preparation and handling, and provides an easy and practical method allowing for a complete blood cell count to be determined from a small volume of sample. The sample can be a saliva sample, or a small blood sample obtained with a finger-prick (FIG. 1). The use of very small amounts of blood for blood count not only reduces the discomfort of the method to a subject, it makes the overall procedure simpler, convenient, and more efficient.

Devices and systems of the invention are compact and portable, thereby allowing for the analysis of a sample in a variety of locations. In some embodiments, the invention allows for the monitoring of a subject without requiring the subject to visit a clinic or a laboratory. For example, the portable quality of the devices of the invention allows a subject to provide a sample and to obtain a complete blood cell count without leaving their home or office. In some embodiments, the invention allows for the health monitoring of a subject at home by the subject's physician.

The invention reduces the complexities of sample preparation and handling required by analysis in a flow-based device. The kits, systems, and devices of the invention include slides and chambers configured for the analysis of a body fluid. Such slides and chambers can be pre-packaged, or not, with a series of reagents capable of detecting and identifying an analyte or a cell type in a body fluid. In some embodiments, a reagent capable of detecting an analyte or a cell type is pre-packaged within a slide or chamber of the invention. The pre-packaging of the reagents within slides can provide a single-step processing step that reduces the complexity of sample preparation. In some embodiments, a reagent capable of detecting an analyte or a cell type is not pre-packaged within a slide or chamber of the invention. A reagent can be provided as a "stock" that can be readily combined with a body fluid and added to a chamber of the invention. A slide and a chamber of the invention can be utilized for immediate analysis of a blood sample by an imaging system, or they can be stored and submitted for later review by, for example, a pathologist.

An imaging system can be configured for acquiring a visual image of a body fluid within a chamber or within multiple chambers in a slide. Imaging systems can be significantly smaller, more portable, and more robust than flow systems. The invention can utilize high quality, inexpensive camera sensors, to acquire high quality visual data from a slide or chamber. A system of the invention can be configured to provide an analysis of the acquired visual image. Large field of view images can be recorded using inexpensive instrumentation. In some embodiments, cell phone image sensors, coupled with lens-free holographic reconstruction or sparse reconstruction techniques, can be used to image large areas in both bright field and fluorescent modalities, with resolutions approaching those of conventional microscope objectives. Cells can be tracked, for example, with submicron precision over a 17 mm$^3$ imaging volume, highlighting the quality of measurements made with inexpensive equipment. Images can be recorded with 24 mm$^2$ fields of view and 600 nm resolution using consumer-grade camera sensors. In some embodiments the sensors can be disposable.

A system of the invention provides the efficiency of automated hematology analysis with the diligence of traditional image-based cytology. A system of the invention allows imaging of cells inside culture chambers and provides an analysis of the cell types within the chamber. In some embodiments, the system, devices, and methods of the invention couples the acquisition and analysis of low-resolution images with specifically designed data analysis methods that provide an accurate counting of red cells, white cells, and platelets, as well as give an accurate 3 part differential for white cells. In some embodiments, the invention comprises kits, systems, devices, and methods that provide a complete blood cell count within the confidence-intervals achieved with clinical instrumentation.

Devices and Systems.

Abnormal results on a complete blood cell count analysis can indicate a plurality of health conditions, including infections, organ transplant rejection, cardiac disease, autoimmune disease, leukemia, anemia, inflammation, and cancer. The current invention provides devices and systems that can be used to analyze a body fluid of a subject in a simple, accurate, and inexpensive way. Non-limiting examples of body fluids include blood, whole blood, serum, plasma, saliva, urine, milk, mucus, and phlegm.

FIG. 1 illustrates devices and systems 10 for performing an analysis of a body fluid, such as a blood or a saliva sample. System 10 illustrates a body fluid collection and holding slide 100 and an automated portable slide analyzer 150. Slide 100 is configured to receive a body fluid from, for example, a blood droplet D collected from a finger prick P on a subject's finger F. In some embodiments, about 1 μL to about 5 μL of body fluid are provided to slide 100. Slide 100 can be configured to receive various of volumes of a body fluid, for example, slide 100 can be configured to receive from about 1 μL to about 5 μL, from about 5 μL to about 10 μL, from about 10 μL to about 15 μL, from about 15 μL to about 20 μL, from about 20 μL to about 25 μL, from about 25 μL to about 30 μL, from about 30 μL to about 35 μL, from about 35 μL to about 40 μL, from about 40 μL to about 45 μL, from about 45 μL to about 50 μL, from about 50 μL to about 55 µL, from about 55 µL to about 60 µL, from about 60 µL to about 65 µL, from about 65 µL to about 70 µL, from about 70 µL to about 75 µL, from about 75 µL to about 80 µL, from about 80 µL to about 85 µL, from about 85 µL to about 90 µL, from about 90 µL to about 95 µL, or from about 95 µL to about 100 µL of body fluid. In some embodiments, about 2 µL of body fluid are provided to slide 100. In some embodiments, the body fluid is blood. In some embodiments, the body fluid is saliva. Slide 100 can have a plurality of chambers and shapes. Slide 100 can be rectangular, circular, elliptical, round, or have other shapes. Slide 100 can have 1 chamber, 2 chambers, 3 chambers, 4 chambers, 5 chambers, 6 chambers, 7 chambers, 8 chambers, 9 chambers, or 10 chambers. In some embodiments, slide 100 can consist of a single chamber. Distinct chambers on a slide can be separated by a distance, for example a distance between about 4 microns to about 100 microns with a port for the insertion of a body fluid. In some embodiments, the slide is configured to have a channel, wherein the channel is in communication with at least one chamber.

Slide 100 can be pre-packaged with a dye solution, a lysing solution, and other compounds. Microfluidics and capillary action can be used to control the flow of a blood sample into the test chambers. A chamber in slide 100 can be pre-packaged with a reagent that interacts with one, or more analytes. In some embodiments, each chamber of slide 100 is pre-packaged with distinct reagents.

The slide 100 can be fabricated, for example, with optically clear glass, plastic, or polycarbonate substrates. Slide 100 can be coated with one, or a plurality of coats that increase a hydrophilicity of the slide. The surfaces of the various sampling chambers of slide 100 can be pre-treated in various ways. In some embodiments the surface can be pre-treated to provide a hydrophilic environment. Hydrophilic surfaces can facilitate the flow of a body fluid sample into one or a plurality of chambers through a channel across a surface of the slide. Hydrophilic surfaces can allow small volumes of a body fluid, such as blood or saliva, to spread out over relatively large areas, for example, a chamber that has a relatively large surface area and a relatively small height.

In some embodiments, the invention comprises an imaging system configured to acquire visual data from the slide. An imaging system can acquire visual data from the slide 100. A transmitter can transmit the acquired visual data to one or a plurality of receivers in a plurality of geographic locations using wireless networks, cell phone networks, or the internet. A transmitter can transmit the acquired visual data over a distance of at least 1 mile, at least 2 miles, at least 3 miles, at least 4 miles, at least 5 miles, at least 7 miles, at least 10 miles, at least 25 miles, at least 50 miles, at least 100 miles, at least 250 miles, at least 500 miles, or at least 1000 miles. In some embodiments, a transmitter wirelessly transmits the acquired visual data over a distance of at least one mile. In some embodiments, a transmitter wirelessly transmits the acquired visual data over a distance of at least ten miles.

In some embodiments, the invention comprises an automated portable slide analyzer configured to analyze visual data from the slide. The automated portable slide analyzer 150 can comprise a display 160 and a control panel 170. Once a blood sample is collected by the slide 100, the slide 100 can be placed into, for example, the portable slide analyzer 150, and the slide 100 can be placed on the slide receiver 155. In some embodiments, the portable slide analyzer can analyze visual data, such as images that can be formed from the visual data. A result of the analysis can be shown on the display 160 of the slide analyzer 150. The slide analyzer can be operated by the control panel 170, but operation of the system 10 can also be automated such that operating the system 10 using the control panel 170 is not necessary.

Figure 2:
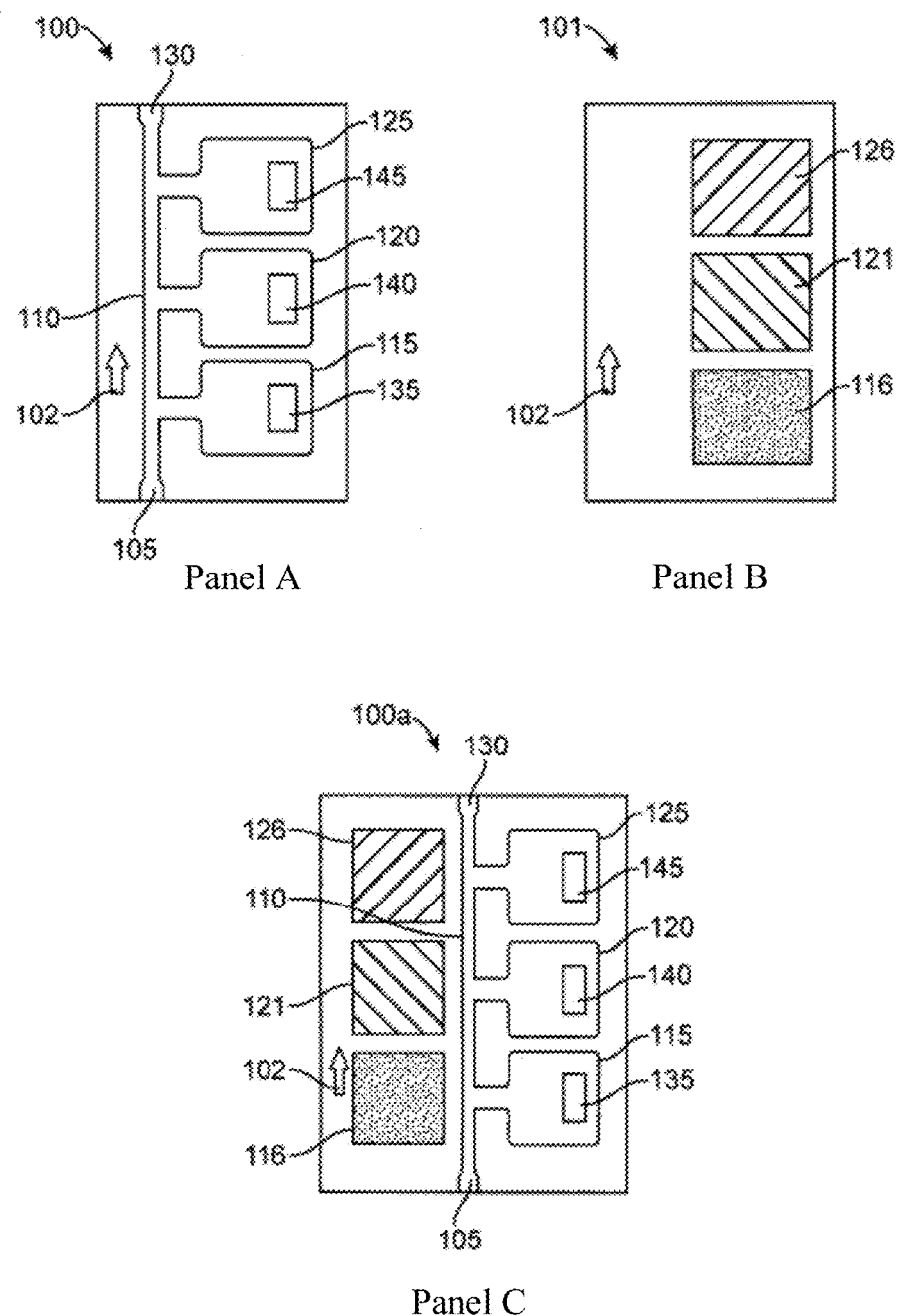
FIG. 2 illustrates slides for analyzing a body fluid. Panel A illustrates a channel in connection with chambers in the slide. Panel B illustrates a slide comprising control chambers. Panel C illustrates a slide comprising a plurality of chambers for the analysis of a body fluid.

FIG. 2 illustrates slides for analyzing a body fluid. Panel A illustrates a channel in connection with chambers in the slide. Panel B illustrates control chambers. Panel C illustrates a slide comprising a plurality of chambers for the analysis of a body fluid and control chambers. Panel A illustrates an example of a slide 100 comprising a port 105, a fluid channel 110, an optional suction port 130, and at least two sampling chambers. Panel A illustrates a first sampling chamber 115, a second sampling chamber 120, and a third sampling chamber 125. In some embodiments, a blood fluid is provided to slide 100 at a port 105 and the body fluid flows through capillary action into the sampling chambers 115, 120, and 125. Slide 100 can comprise a marking 102 to indicate an orientation of the first chamber relative to part 105. In some embodiments, marking 102 further indicates a proper direction for placing slide 100 into a slide analyzer 150. Each sampling chamber can be analyzed for different analytes, for example, different types of blood cells. The first sampling chamber 115, for example, can be configured for the analysis of red blood cells, the second sampling chamber 120 can be configured for the analysis of white blood cells, and the third sampling chamber 125 can be configured for the analysis of platelets.

Each sampling chamber can be pre-packaged with one or more reagents. A reagent can be pre-packaged into a sampling chamber as a solution or as a dry powder. A reagent can include a surfactant to facilitate an analysis of a body fluid in a sample. A reagent can mix with an analyte that is being channeled into, for example, sampling chambers 115, 120, or 125. In some embodiments, a first sampling chamber 115 can contain, for example, a first dry form reagent 135, the second sampling chamber 120 can contain a second dry form reagent 140, and the third sampling chamber 125 can contain a third dry form reagent 145. In some embodiments, a first sampling chamber 115 can contain, for example, a first liquid form reagent 135, the second sampling chamber 120 can contain a second liquid form reagent 140, and the third sampling chamber 125 can contain a third liquid form reagent 145. In some embodiments, slide 100 comprises a combination of dry and liquid reagents.

A chamber can comprise a diluent, a dye, and other chemical compounds. A dilution can provide an optimum concentration for the analysis of an analyte with a reagent. A chamber can be in fluid communication with one or a plurality of chambers through a common channel or a chamber can be physically isolated from other chambers. A body fluid can be diluted by a reagent present in a chamber and a body fluid can be diluted prior to being provided to a chamber. A dilution can be a serial dilution, which can result in a geometric progression of the concentration in a logarithmic fashion. For example, a ten-fold serial dilution can be 1 M, 0.1 M, 0.01 M, 0.001 M, and a geometric progression thereof. A dilution can be, for example, a one-fold dilution, a two-fold dilution, a three-fold dilution, a four-fold dilution, a five-fold dilution, a six-fold dilution, a seven-fold dilution, an eight-fold dilution, a nine-fold dilution, a ten-fold dilution, a sixteen-fold dilution, a twenty-five-fold dilution, a thirty-two-fold dilution, a sixty-four-fold dilution, and/or a one-hundred-and-twenty-five-fold dilution. In some embodiments, dilution of a body fluid is not required for analysis of an analyte or cell type with a reagent and a drop of a body fluid is provided directly to a part within a slide of the invention.

A device and a system of the invention can be used to analyze a body fluid that is spread across a surface area of a slide or chamber. A surface area of a chamber can be from about 0.1 mm$^2$ to about 0.5 mm$^2$, from about 0.1 mm$^2$ to about 1 mm$^2$, from about 1 mm$^2$ to about 5 mm$^2$, from about 5 mm$^2$ to about 10 mm$^2$, from about 10 mm$^2$ to about 15 mm$^2$, from about 15 mm$^2$ to about 20 mm$^2$, from about 20 mm$^2$ to about 25 mm$^2$, from about 25 mm$^2$ to about 30 mm$^2$, from about 30 mm$^2$ to about 35 mm$^2$, from about 35 mm$^2$ to about 40 mm$^2$, from about 40 mm$^2$ to about 45 mm$^2$, from about 45 mm$^2$ to about 50 mm$^2$, from about 50 mm$^2$ to about 55 mm$^2$, from about 55 mm$^2$ to about 60 mm$^2$, from about 60 mm$^2$ to about 65 mm$^2$, from about 65 mm$^2$ to about 70 mm$^2$, from about 70 mm$^2$ to about 75 mm$^2$, from about 75 mm$^2$ to about 80 mm$^2$, from about 80 mm$^2$ to about 85 mm$^2$, from about 85 mm$^2$ to about 90 mm$^2$, from about 90 mm$^2$ to about 95 mm$^2$, or from about 95 mm$^2$ to about 100 mm$^2$.

In some embodiments, a device of the invention weighs less than 50 pounds, less than 49 pounds, less than 48 pounds, less than 47 pounds, less than 46 pounds, less than 45 pounds, less than 44 pounds, less than 43 pounds, less than 42 pounds, less than 41 pounds, less than 40 pounds, less than 39 pounds, less than 38 pounds, less than 37 pounds, less than 36 pounds, less than 35 pounds, less than 34 pounds, less than 33 pounds, less than 32 pounds, less than 31 pounds, less than 30 pounds, less than 29 pounds, less than 28 pounds, less than 27 pounds, less than 26 pounds, less than 25 pounds, less than 24 pounds, less than 23 pounds, less than 22 pounds, less than 21 pounds, less than 20 pounds, less than 19 pounds, less than 18 pounds, less than 17 pounds, less than 16 pounds, less than 15 pounds, less than 14 pounds, less than 13 pounds, less than 12 pounds, less than 11 pounds, less than 10 pounds, less than 9 pounds, less than 8 pounds, less than 7 pounds, less than 6 pounds, less than 5 pounds, less than 4 pounds, less than 3 pounds, less than 2 pounds, or less than 1 pound. A device of the invention can have a minimum weight of about 4 ounces, about 8 ounces, about 12 ounces, about 1 pound, about 1.5 pounds, or about 2 pounds.

In some embodiments, a device has a total mass of less than 5,000 g, less than 4,000 g, less than 3,000 g, less than 2,000 g, less than 1,500 g, less than 1,400 g, less than 1,300 g, less than 1,200 g, less than 1,100 g, less than 1,000 g, less than 900 g, less than 800 g, less than 700 g, less than 600 g, or less than 500 g. A device of the invention can have a minimum total mass of about 100 g, about 200 g, about 300 g, about 400 g, or about 500 g.

A device of the invention can have various shapes and dimensions. A device of the invention can be, for example, a cube, a cylinder, a cone, a sphere, a pyramid, or have other shapes. A device of the invention can have a height (H), width (W), or depth (D), each independently of about 1 inch, about 2 inches, about 3 inches, about 4 inches, about 5 inches, about 6 inches, about 7 inches, about 8 inches, about 9 inches, or about 10 inches. In some embodiments, a device of the invention is a cube. The dimensions can be, for example, 6" H×6" W×6" D, or less than 6" H×6" W×6" D.

A chamber can contain a reagent that is capable of detecting an analyte or a cell type. In some embodiments, a chamber can comprise a lysing reagent. A lysing reagent can be, for example, sodium dodecyl sulfate (SDS), saponins, snake venom, quaternary ammonium salts, triton-X, or other lysing agents. In some embodiments, a chamber can comprise a reagent that is a fluorophore, for example, a nucleic acid stain such as Acridine Orange, 7-AAD, hydroxystilbamidine, or LDS 751. In some embodiments, a chamber can comprise 0.1 mM to 0.3 mM of SDS in a phosphate buffered saline (PBS) buffer. In some embodiments, a reagent can be a fixative. Detection of a cell type or analyte with a reagent in a chamber can facilitate the analysis of a body fluid. Non-limiting examples of a fixative include aldehydes, such as formaldehyde and glutaraldehyde, and alcohols, such as ethanol and methanol.

A device and a system of the invention can comprise a calibration slide. FIG. 2 panel B illustrates a calibration slide 101. The calibration slide 101 can comprise one or more calibration chambers, for example, a first calibration chamber 116, a second calibration chamber 121, and a third calibration chamber 126. A calibration chamber 116, 121, or 126 can include a predetermined number of cell types, analytes, or other possible standards with properties similar to those of the body fluid. A calibration slide can comprise a standard with a similar size and fluorescent properties as, for example, a blood sample. A calibration slide can comprise polystyrene beads or cell reproductions that can be painted or printed onto the bottom of calibration chambers 116, 121, or 126. In some embodiments, a calibration chamber 116 can include a predetermined number of reproductions of red blood cells, a calibration chamber 121 can include a predetermined number of reproductions of white bloods cells, and a calibration chamber 126 can include a predetermined number of reproductions of platelets. In some embodiments, a calibration image is acquired by an imaging system configured to acquire visual data from the slide.

In some embodiments, a calibration slide 101 is used to calibrate a slide analyzer 150. To calibrate the slide analyzer 150, the slide analyzer 150 can take an image of a calibration chamber, the image can be analyzed to count the number of cell reproductions, and the counted number can be compared to a predetermined number, such as a standard or reference. The slide analyzer 150 can be adjusted as necessary for calibration purposes. Like with slide 100, the calibration slide 101 can also comprise a marking 102 to indicate the proper orientation and direction of the slide 100 as placed into the slide analyzer 150 (FIG. 2 panel B).

In some embodiments, calibration and body fluid analysis can be performed with the same slide. FIG. 2 panel C shows a blood collection and analysis slide 100a configured for such use. The slide 100a comprises an orientation and directionality indicator marking 102, a port 105, a channel 110, a first chamber 115 having therein a reagent 135, a second chamber 120 having therein a second reagent 140, a third chamber 125 having therein a third reagent 145, an optional suction port 130, a first calibration chamber 116, a second calibration chamber 121, and a third calibration chamber 126.

Figure 3:
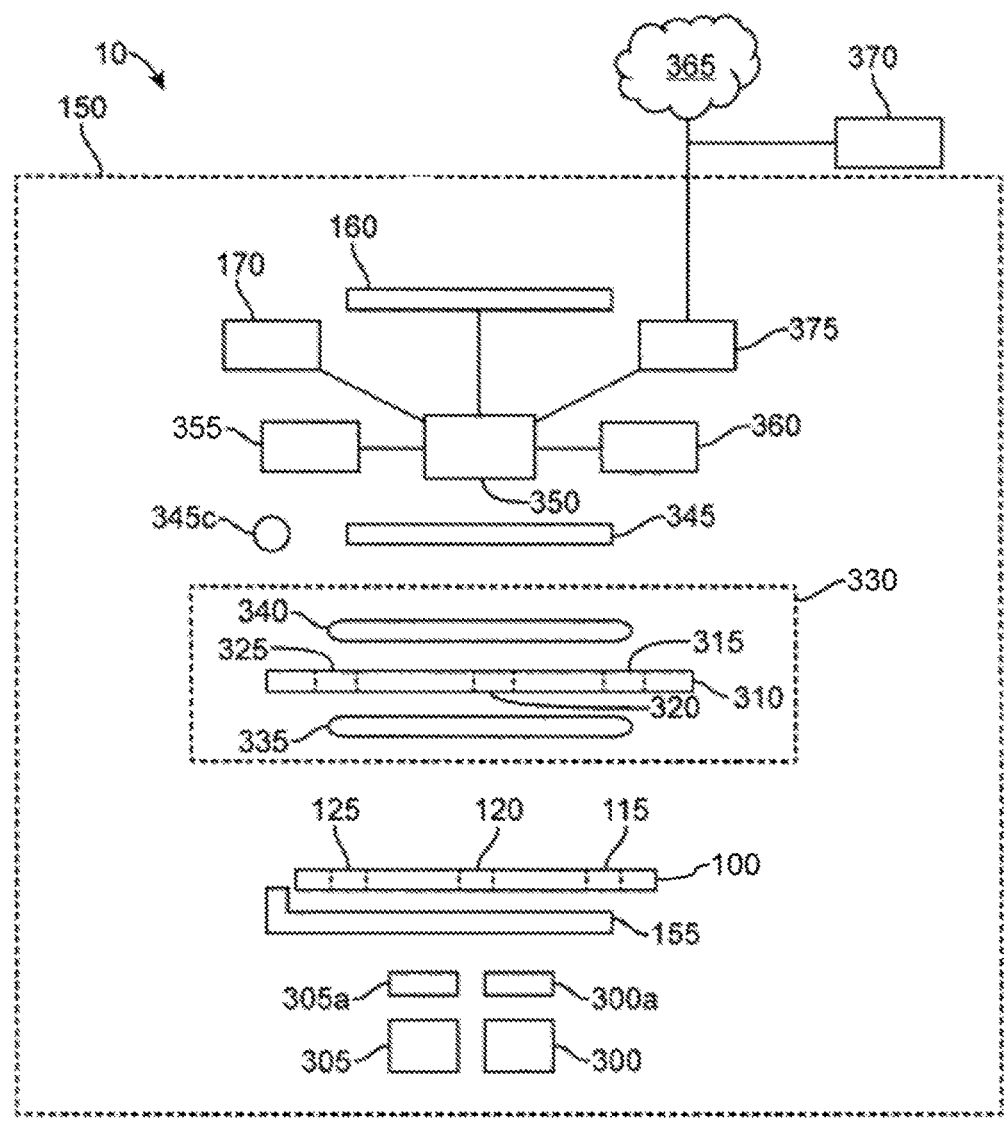
FIG. 3 is a diagram of a system for analyzing a body fluid.

FIG. 3 is a diagram of a system for analyzing a body fluid, and illustrates a system 10 for performing an analysis of a body fluid. FIG. 3 illustrates an embodiment wherein a slide 100 can be inserted into a slide receiver 155 of a slide analyzer 150. The slide receiver 155 can be automatically moveable such that different chambers can be analyzed at different times. Under instructions from a processor 350 of the slide analyzer 150, the slide receiver 155 can move slide 100 so that a first sampling chamber 115, a second sampling chamber 120, and/or a third sampling chamber 125 can be analyzed. If a slide inserted into the slide analyzer 150 has any calibration chambers, the slide receiver 155 can move the slide so that any desired calibration chambers can also be analyzed. In some embodiments, an imaging system can acquire visual data from the slide and transmit the acquired visual data to a receiver. In some embodiments, the processor 350 is further configured to provide an analysis of the visual data.

A slide 100 can be moved inside a slide receiver 155. For example, a slide can be rotated within the slide receiver. In some embodiments, a slide receiver 155 can comprise a micromanipulator capable of moving the slide receiver 155 in small, precise steps. In some embodiments the slide 100 can be sealed or otherwise fluidly isolated from the slide analyzer 150 to minimize the risk of cross-contamination that can arise with repeated uses of the slide analyzer 150. The slide analyzer 150 can also be configured to withstand sterilization and cleaning, for example by exposure to UV or other radiation or to various cleaning and sterilization chemicals, without adversely affecting the function of the slide analyzer 150.

A system of the invention can comprise a plurality of components comprising an imaging system configured to acquired visual data. A system of the invention can comprise a primary light source 300, an optics assembly 304, and an image capture element 345, which can be configured to acquire visual data from slide 100.

FIG. 3 illustrates an embodiment wherein the primary light source 300 is configured to acquire visual data from slide 100. FIG. 3 illustrates a second light source 305 that can be utilized, for example, to support the acquisition of visual images comprising side scatter measurements of any of the sampling chambers of the slide 100. The primary light source 300 illuminates a sampling chamber (for example, the sampling chamber 120 as shown in FIG. 3). Both the primary light source 300 and the secondary light source 305, placed at an angle that can vary against the primary light source based on the type of measurement being performed, can further comprise condenser optics 300a and 305a, respectively, to facilitate the illumination of the slide and its components, such as by facilitating the formation of a parallel illumination beam.

A system 10 can comprise a movable filter assembly 310. A movable filter assembly 310 can comprise one or more filters, such as color filters and spatial filters. Light from the illuminated sampling chamber can pass through one of the filters of the moveable filter assembly 310. As shown in FIG. 3, the movable filter assembly 310 comprises a first filter 315, a second filter 320, and a third filter 325. The first filter 315 can be, for example a red filter, the second filter 320 can be a green filter, and the third filter 325 can be a spatial filter configured to acquire light scatter measurements of visual data. The moveable filter assembly 310 can be moved through instructions from the processor 350 so that a desired filter can be selected to facilitate image capture and analysis. The moveable filter assembly 310 can comprise a micromanipulator capable of moving the moveable filter assembly 310 in small, precise steps. The moveable filter assembly 310 can be a component of the optics assembly 304.

Before passing through a desired filter, light from the sampling chamber can first pass through the other elements of the optics assembly 304. The optics assembly 304 can comprise at least two lenses, a first lens 335 and a second lens 340, which can be used to magnify any visual data taken and to adjust the focal plane of the optics assembly 304. Visual data can, for example, be magnified up from about 3× to about 20×. A system 10 can comprise a moveable filter assembly 310 that is disposed between the first lens 335 and the second lens 340, with light first passing through the first lens 335 before passing the filter assembly 310.

The image from the sampling chamber 120 can be taken by the image capture element 345 after the light of the image passes through the optics assembly 304. The image capture element 345 can comprise a CCD or CMOS detector array, for example, a low-cost, high-resolution CCD. The system 10 can further comprise a cooling element 345c for cooling the image capture element 345. Also, the image capture element 345 and the optics assembly 304 can in many cases be moveable as a unit so that they can scan across various fields in a focal plane of a sampling chamber.

In some embodiments, a system of the invention comprises a slide analyzer 150, wherein the slide analyzer further comprises a processor 350, a memory module 355, a communications module 360, a transmitter 375, a display 160, and a control panel 170. User input can be entered into the slide analyzer 150 through the control panel 170 which in turn sends instructions to the processor 350. The processor 350 can send and receive various instructions, for example, for adjusting the position of the slide receiver 155 to determine which sampling chamber to analyze, for adjusting the position of the filter assembly 310 to determine which light filter to use, for adjusting the magnification and focal plane of the optics assembly 304, or for instructing the image capture element 345 to capture one or more images. The processor 350 can be coupled to a memory module 355 for the storage of captured images. The memory module 355 can comprise a random-access memory (RAM), a flash memory, a hard drive, or other volatile or non-volatile memory. The processor 350 can be coupled to a transmitter 360 which can transmit 365 acquired visual data to various receivers. A transmitter 375 can transmit the acquired visual data in a certified secure transmission, for example, a transmission 365 that is certified by HIPAA (Health Insurance Portability and Accountability Act). The acquired and/or transmitted visual data can be analyzed using image analysis software to determine a cell type, or an analyte, present in a body fluid. Analysis of the visual data can be permanently and automatically recorded in a subject's health records.

A plurality of transmission techniques can be used by a transmitter 375 to transmit the acquired visual data. A transmission can be a wireless transmission or a wired transmission. In some embodiments, processor 350 is configured with computer-program code that can provide an analysis of the visual data. In some embodiments, the transmitted visual data is analyzed by a second system 370. A second system can be, for example, a second computer-system 370. The second system can analyze the transmitted visual image, and the second system can return a result of an analysis data to system 10. The processor 350 can then have the result of a data analysis displayed on the display 160. In some embodiments, the processor 350 can be programmed to perform at least some or even all of the analysis on an acquired image itself and then display the analysis results on the display 160. In some embodiments, analysis of slide 100 with a processor 350 within system 10 does not require access to a transmitter.

After the slide 100 has been analyzed, either directly by an imaging system configured to acquire visual data from the slide, or by a slide analyzer 150, the slide 100 can be disposed of as non-toxic waste, or slide 100 can be preserved for further analysis. A receptacle can optionally be provided and used for the disposal of slides with a kit of the invention.

Figure 4:
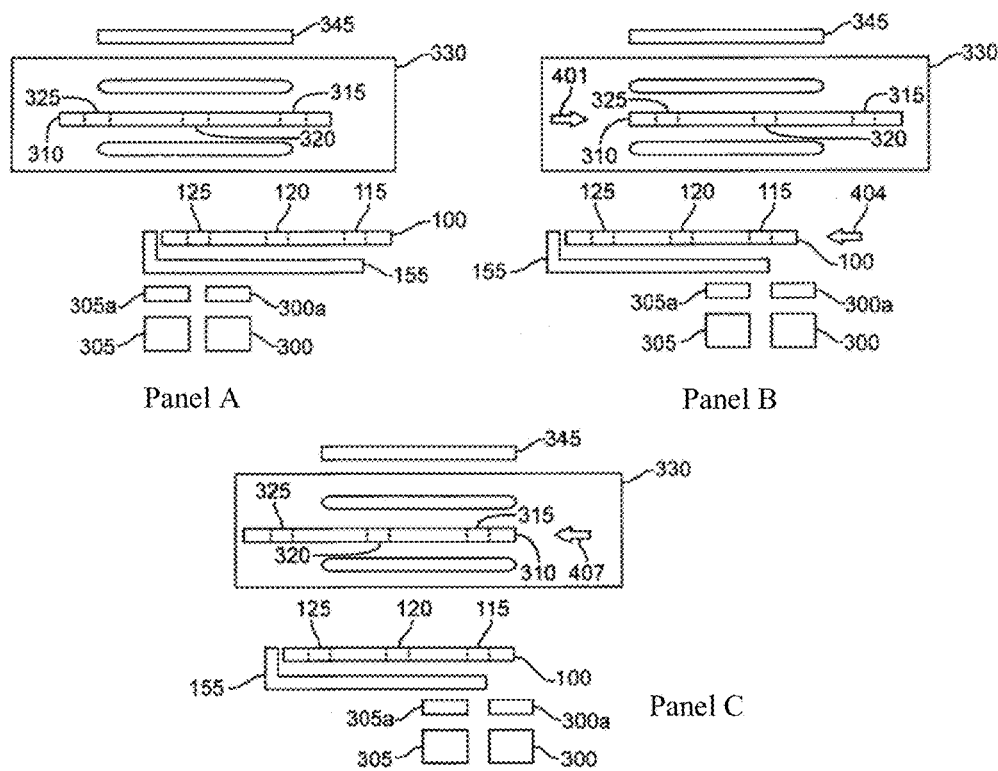
FIG. 4 illustrates a system for analyzing a body fluid with a movable slide and a movable filter assembly. Panel A illustrates how a slide can be positioned in relation to an imaging system. Panels B and C illustrate ways in which a movable filter assembly can be moved.

As discussed above, the filter assembly 310 and the slide receiver 155 with the slide 100 can be selectively moved to select the particular light filter used and the particular sampling chamber to be analyzed. FIG. 4 illustrates a system for analyzing a body fluid with a movable slide and a movable filter assembly. Panel A illustrates how a slide can be positioned in relation to an imaging system. Panels B and C illustrate ways in which a movable filter assembly can be moved.

As shown in FIG. 4 panel A, the slide receiver 155 can be positioned so that the third sampling chamber 125 can be analyzed and the filter assembly 310 can be positioned so that the second filter 320 can be used in the process of acquiring a visual image. As shown in panel B, the filter assembly 310 can be moved in a direction 401 so that the third filter 325 can instead be used and the slide receiver 155 can be moved in a direction 404 so that the second sampling chamber 120 can be analyzed. As shown in panel C, the filter assembly 310 can be moved in a direction 407 so that the first filter 315 can be used. Additionally, any number of combinations of particular filters on the filter assembly 310 and particular sampling chambers of the slide 100 can be moved into optical alignment.

Methods of the Invention.

Methods and processes for the analysis of a body fluid can provide an overview of a subject's general health status. For example, a complete blood cell count can provide information about the cells in a subject's blood. Abnormally high or low counts may indicate the presence of many forms of disease, and hence blood counts are amongst the most commonly performed blood tests in medicine. Methods and processes for the analysis of a body fluid usually require multiple-step protocols. For example, representative methods for acquiring a complete blood cell count often require lysis of an excess of red blood cells in order to obtain accurate counts. Furthermore, white cell differentiation is often accomplished using a combination of dyes that need to be handled in a specific manner, for instance, antibody conjugated dyes for use in a white cell differentiation can be provided as a concentrated stock that needs to be kept within specific temperatures until use.

The system of the invention, by contrast, provides a practical and accessible method for the analysis of a body fluid, such as blood or saliva. A method of the invention can comprise diluting sub-microliter volumes of whole blood into a diluent within a slide (or chamber), and placing the slide within an acquisition range of an imaging system configured to acquire visual data from the slide for an analysis. A diluent can be a phosphate buffered saline buffer comprising a nucleic acid dye, such as acridine orange (AO), and an anionic surfactant, such as sodium dodecyl sulfate (SDS). In some embodiments, the invention effectively provides a method for using a dilution to form a uniform monolayer of cells at the bottom of a slide or chamber and for using a fluorescent dye to stain white cells and platelets to differentiate them from red cells.

Because red cells have a disc-like shape that may have random orientations within a cell chamber, it is a computationally difficult task to count unprepared red blood cells. Therefore, a second reagent, sodium dodecyl sulfate (SDS), is used to sphere red blood cells. SDS is an anionic surfactant that reduces the surface tension of red cell membranes. When added to blood in an appropriate concentration, it acts to isovolumetrically sphere the cells, causing them to lose their biconcave disk shape and become uniform spheres. The sphered red blood cells pack in a monolayer in a uniform fashion, and their consistent shape allows them to be easily and accurately counted using simple visual data processing techniques. A suitable visual data can be acquired with an imaging system of the invention. In some embodiments, the invention effectively provides a method for an analysis of a red blood cell in a sample, wherein a sphering of the red blood cell minimizes variability of red blood cells images in visual data due to blood cell orientation.

A diluent can be used to provide an accurate count of white blood cells, platelets, and sphered red blood cells. A diluent can be used to control the density of blood cells within a slide or within a chamber, and a diluent can be used to form a monolayer of cells inside the chamber. A method of the invention can provide an accurate count of all red blood cells within a single image, when the cells are able to settle and to form a monolayer in the chamber. A dilution factor can be optimized to simultaneously provide, for example, an analysis of red blood cells, and white blood cells in a body fluid. Since white blood cells are approximately 1000 times less numerous in whole blood as compared to red blood cells, a dilution factor can be optimized such that a sufficient number of white blood cells are counted. In some embodiments, a 5 to 10 fold dilution of whole blood provides a monolayer of cells that is suitable for a simultaneous analysis of red blood cells and white blood cells.

A body fluid within a slide or chamber can be analyzed with a reagent comprising a single and stable dye that has a natural affinity for nucleic acids. A stable dye can be, for example, acridine orange. When binding to DNA, acridine orange intercalates with the DNA as a monomer and yields intense green fluorescence under blue excitation. When binding to RNA and proteins it forms an electrostatic complex in a polymeric form that yields red fluorescence under blue excitation. Because bound acridine orange fluoresces more intensely than the unbound dye, staining of a body fluid with a method of the invention does not require a washing step. Since different white blood cell types have different amounts of DNA and RNA, a white blood cell population can yield different relative amounts of red and green fluorescence. This allows separation of cell type based on their color. Since platelets are often characterized by a small amount of RNA, platelets can be faintly stained with acridine orange. The small amount of RNA within platelets allows for the detection of platelets with a method of the invention. In some embodiments, a method of the invention allows for the determination of a complete blood cell count in a small amount of body fluid.

In some embodiments, analysis of a sample utilizes about 0.5 nL to about 50 nL of body fluid, about 1 nL to about 100 nL of body fluid, about 100 nL to about 150 nL of body fluid, about 150 nL to about 200 nL of body fluid, about 200 nL to about 250 nL of body fluid, about 250 nL to about 300 nL of body fluid, about 300 nL to about 350 nL of body fluid, about 350 nL to about 400 nL of body fluid, about 400 nL to about 450 nL of body fluid, about 450 nL to about 500 nL of body fluid, about 500 nL to about 550 nL of body fluid, about 550 nL to about 600 nL of body fluid, about 600 nL to about 650 nL of body fluid, about 650 nL to about 700 nL of body fluid, about 700 nL to about 750 nL of body fluid, about 750 nL to about 800 nL of body fluid, about 800 nL to about 850 nL of body fluid, about 850 nL to about 900 nL of body fluid, about 900 nL to about 950 nL of body fluid, about 950 nL to about 1 µL of body fluid, about 0.5 µL to about 1 µL of body fluid, about 1 µL to about 5 µL of body fluid, about 5 µL to about 10 µL of body fluid, about 10 µL to about 20 µL of body fluid, about 20 µL to about 30 µL of body fluid, about 30 µL to about 40 µL of body fluid, or about 40 µL to about 50 µL of body fluid.

In some embodiments, a method of the invention can analyze a small volume of body fluid that is, for example, spread across a surface area as a monolayer. A small volume of body fluid can be less than about 100 nL of body fluid, less than about 200 nL of body fluid, less than about 300 nL of body fluid, less than about 400 nL of body fluid, less than about 500 nL of body fluid, less than about 600 nL of body fluid, less than about 700 nL of body fluid, less than about 800 nL of body fluid, less than about 900 nL of body fluid, less than about 1 µL of body fluid, less than about 2 µL of body fluid, less than about 3 µL of body fluid, less than about 4 µL of body fluid, less than about 5 µL of body fluid, less than about 6 µL of body fluid, less than about 7 µL of body fluid, less than about 8 µL of body fluid, less than about 9 µL of body fluid, or less than about 10 µL of body fluid.

Acquiring a Visual Image.

Once the body fluid is appropriately diluted within a chamber, or within a slide comprising two or more chambers, a visual image of the body fluid can be acquired and analyzed. In some embodiments, a method of the invention comprises diluting blood samples in a single diluent comprising phosphate buffered saline, sodium dodecyl sulfate, and acridine orange, followed by acquisition of visual data from the body fluid with fluorescence and dark field imaging using, for example, low magnification objectives. In some embodiments, an analysis of the acquired visual image provides a complete blood cell count of a sample.

Visual images can be taken with, for example, a halogen bulb, a dark-field condenser, and a large format camera. Visual image acquisition can comprise acquiring a combination of dark-field and fluorescence visual images to count and differentiate white blood cells, platelets, and red blood cells within, for example, one chamber. In some embodiments one visual image is acquired. In some embodiments, pluralities of visual images are acquired. An imaging system of the invention can acquire, for example, at least one dark-field visual image, at least two dark-field visual images, at least three dark-field visual images, at least four dark-field visual images, at least five dark-field visual images, at least six dark-field visual images, at least seven dark-field visual images, at least eight dark-field visual images, at least nine dark-field visual images, or at least ten dark-field visual images. An imaging system of the invention can acquire, for example, at least one bright-field visual image, at least two bright-field visual images, at least three bright-field visual images, at least four bright-field visual images, at least five bright-field visual images, at least six bright-field visual images, at least seven bright-field visual images, at least eight bright-field visual images, at least nine bright-field visual images, or at least ten bright field visual images. An imaging system of the invention can acquire, for example, at least one fluorescent visual image, at least two fluorescent visual images, at least three fluorescent visual images, at least four fluorescent visual images, at least five fluorescent visual images, at least six fluorescent visual images, at least seven fluorescent visual images, at least eight fluorescent visual images, at least nine fluorescent visual images, or at least ten fluorescent visual images. An imaging system of the invention can acquire any combination of dark field, bright field, or fluorescent visual images. In some embodiments, bright-field visual images or dark-field visual images are used for imaging red blood cells. In some embodiments, 1-channel fluorescent visual images or 2-channel fluorescent visual images are used for imaging white blood cells or platelets. In some embodiments, a final image product includes data from at least three images.

An imaging system of the invention can be configured to acquire two-channel fluorescent visual images of a cell type. For example, visual images comprising white cells can be acquired using a 4× objective and 470 nm excitation light, with the red and green channels being acquired sequentially by changing emission filters placed in front of the camera automatically. The entirety of a cell chamber can be imaged, for example, by moving the chamber and tiling image fields together.

An imaging system of the invention can be configured to acquire one-channel fluorescent visual images of a cell type. For example, a visual image comprising a platelet cell can be acquired with a 10× objective lens. In some embodiments, a visual image of a platelet can be acquired with the same excitation source and red emission filter as utilized for acquiring a visual image of a white blood cell. In some embodiments, dark-field images of different cell types can be taken using the same objective lens. For example, dark-field images of red blood cells and white blood cells can be taken at the same excitation using, for instance, a 4× objective lens.

A visual image can be acquired from a segment of a surface area of a chamber, or a visual image can be acquired from the entirety of the surface area of a chamber. In some embodiments, the density of a cell population is associated with the number of visual images required for an analysis. For example, a single image taken from the center of the counting chamber sufficed to provide consistent visual information for an accurate analysis of a red blood cell population. In contrast, at least two visual images from different surfaces of the chamber can be required for an analysis of a platelet population. Representative images taken using the devices, systems, and methods of the invention are shown and described in further detail in FIG. 10. Visual data can be transmitted to a receiver. In some embodiments, the receiver is in communication with a computer system comprising a processor, wherein the computer system is programmed to perform an analysis of the visual data.

Data Analysis.

To provide a complete blood cell count (including any or all of red blood cells, white blood cells, and platelets) from an acquired visual image, a system of the invention can utilize an algorithm that identifies and quantifies individual cell types from the visual data. To determine whether a particular object in the visual data is, for example, a white blood cell, the system can identify a set of visual images acquired, for example, with a particular filter and/or within a particular emission wavelength. A system can group the set of acquired visual data based on a fluorescence. A mean or median fluorescence intensity from a particular image can be subtracted from a reference image comprising a background fluorescence signal. Cell regions can then be identified using thresholding or watershed segmentation, and the mean channel intensities for each cell can be computed.

Once identified, a cell can be counted. For example, the number of red or white blood cells or platelets in one image or a set of images can be identified by comparison with various reference images present in a reference database. Once the number of red or white blood cells or platelets is counted, subpopulations and related percentages can be determined. Different subpopulations can be grouped according to their range of fluorescent responses across two or more frequencies. In addition, mixed Gaussian modeling of two-dimensional histograms of green and red fluorescent intensities can be generated and analyzed. Higher dimension histograms, for example, histograms including fluorescent intensities at different wavelengths or wavelength ranges and light scatter measurements, can also be created and analyzed. To analyze the data, principal component decomposition on this multidimensional data can be performed and at least one dimension can be fitted into, for example, Gaussian models, skew-T models, or log-normal models.

Data mining techniques and algorithms, such as supervised or unsupervised clustering techniques, can be applied to the identification and enumeration of cell subpopulations.

A Fourier transform or other mathematical transformations can be performed on an acquired visual image to obtain a diffraction pattern of the body fluid in a slide that can be used in a data analysis. A diffraction pattern can be analyzed to determine, for example, a distribution of cell radii. Based on the cell radii, the volume distribution of the red blood cells, the mean cell volume (MCV), and the red blood cell distribution width (RDW) can be determined from the visual image. In some embodiments, the volume of the sample size provided to the chamber is known, and the MCV and RBC can be used to determine a hematocrit (HCT) count.

A data analysis of the acquired visual image can comprise a template matching of the visual image. For example, bright field or dark field images of unstained blood can be acquired with an imaging system, and the acquired visual data can be compared to the visual data in a reference database. Visual data can be acquired and analyzed at low magnifications and high magnifications. For example, at high magnifications, platelets can be visible in an image as tiny dust-like objects that are distinguishable from other cells based on size.

Data analysis with the method and system of the invention can identify a plurality of populations and subpopulations of blood cells. For example, an analysis can identify the mean corpuscular hemoglobin concentration (MCHC) of a sample. A blood sample can be imaged using multiple wavelengths, or wavelength ranges of light and the average absorption of light by a cell type can be computed. A computer system can apply, for example, a Beer-Lambert Law model to the sphered shape of the blood cells and determine a MCHC.

Conditions that can be Detected with a Complete Blood Cell Count.

A complete blood count provides important information regarding the types and numbers of cells in the blood, especially red blood cells, white blood cells, and platelets. A CBC can help a physician identify physiological causes of conditions, such as weakness, fatigue, bruising, or a cancer. A CBC can be used to diagnose a condition, such as anemia, infection, or cancer. A CBC can allow a clinician to monitor a physiological response of a subject to a treatment and a CBC can allow a subject to monitor a subject's own response to a treatment. A CBC can provide an analysis of a white blood cell, a red blood cell, and a platelet population of a subject.

Common abnormalities that can be diagnosed in clinical practice with a complete blood cell count include anemia, polycythemia, leukopenia, leukocytosis, and thrombocytopenia. Non-limiting examples of common types of anemias that can be diagnosed with a CBC include iron-deficiency anemia, thalassemias, hemoglobinopathies (like sickle cell anemia), medication-related anemias, and chronic disease-related anemias.

White blood cells have an important physiological role in protecting a subject against infection. When a subject has an infection, for example, a bacterial infection, the number of white blood cells rises very quickly. The number of white blood cells can therefore be used to determine a physiological response to a malignancy or treatment. A total count of leukocytes in circulation and a determination of a leukocyte differential can provide a diagnosis of several hematologic malignancies, such as leukemias.

Red blood cells carry oxygen from the lungs to the rest of the body, and carbon dioxide back to the lungs for expiration. If the RBC count is low, for example, in the case of anemia, a subject's body can be deprived of oxygen. If the count is too high, a condition called polycythemia, the red blood cells can clump together and block capillaries and blood vessels. Therefore, determining the amount of hemoglobin in a subject's blood with a CBC can provide an analysis of the blood's ability to carry oxygen throughout the body.

Platelets are the smallest formed element in blood. They are important in, for example, blood clotting, atherosclerosis, and thrombocytopenia. When bleeding occurs, platelets swell, clump together, and form a sticky plug that helps prevent bleeding. A subject with too few platelets can suffer from uncontrolled bleeding. A blood clot formed from too many platelets can clog a blood vessel.

With the aid of the invention, a clinician can remotely receive a complete blood cell count that is transmitted by a system of the invention to the clinician. Consequently, a clinician can monitor a subject's response to a treatment without requiring the subject to visit a clinic or a hospital. A clinician can be, for example, a physician, a nurse, a nurse practitioner, or an individual responsible for monitoring the health of a subject. Subjects can be, for example, elderly adults, adults, adolescents, pre-adolescents, children, toddlers, infants. The invention provides systems, devices, and methods that can be utilized by a subject to monitor a subject's response to a treatment, or to monitor a subject's health. The invention provides systems, devices, and methods that can be utilized by a clinician to monitor a subject's response to a treatment, or to monitor a subject's health.

EXAMPLES

Example 1: Methods of the Invention

Flowchart 500 (FIG. 5) illustrates a method for analyzing a body fluid comprising the steps of providing the body fluid to a chamber, detecting an analyte in the body fluid with a reagent, acquiring visual data from the slide, and analyzing the visual data. The example illustrates a representative embodiment wherein the body fluid is a blood sample.

In 505 a subject provides a small volume of blood sample to a chamber. A subject can use a finger-prick needle to penetrate the skin and to retrieve a drop of blood. A relatively small volume of blood is required, and a drop of blood can be, for example, a sub-microliter volume of blood or a volume of blood between about 1 μL and about 5 μL. The subject can add the drop of the blood to a chamber, such as the chambers described herein 510.

A chamber can be pre-packaged with a reagent that stains the blood sample 515. The reagent can comprise, for example, a fluorescent dye, such as acridine orange, and a surfactant, such as sodium dodecyl sulfate (SDS). The stained sample can be illuminated 520, for example, with a light source 300 as previously described. The sample can be illuminated at a first wavelength and an imaging system can acquire visual data from the illuminated sample 525. A fluorescent response of the stained sample at a first wavelength or wavelength range can be measured by an imaging system. For example, the first wavelength can excite a fluorophore associated with a cell type within the chamber, such as acridine orange. Excitation of a fluorophore and acquisition of the visual image can provide a visual image associated with a concentration of DNA in a particular cell type or analyte. A second wavelength can be used to illuminate the sample and an imaging system can acquire visual data from the sample illuminated with the second wavelength 530. The fluorescent emission of the stained sample at additional wavelengths using one or more additional light sources emitting at different wavelengths can also be measured. Bright-field and dark-field images of the blood sample can also be acquired by an imaging system. An imaging system 525 and 530 configured to acquire visual data from the chamber can be configured to magnify a field with a lens prior to acquiring the image. 525 and 530 can acquire visual data from a field or a plurality of fields that can be added and merged together during an analysis of the visual data.

The acquired visual data can be grouped and analyzed 535. For example, a set of visual data can be grouped based on a wavelength used to illuminate the chamber. Grouping of the acquired visual data can provide a merging of the images. An analysis of the visual data by a computer-program product can provide a complete blood cell count 540.

Figure 5:
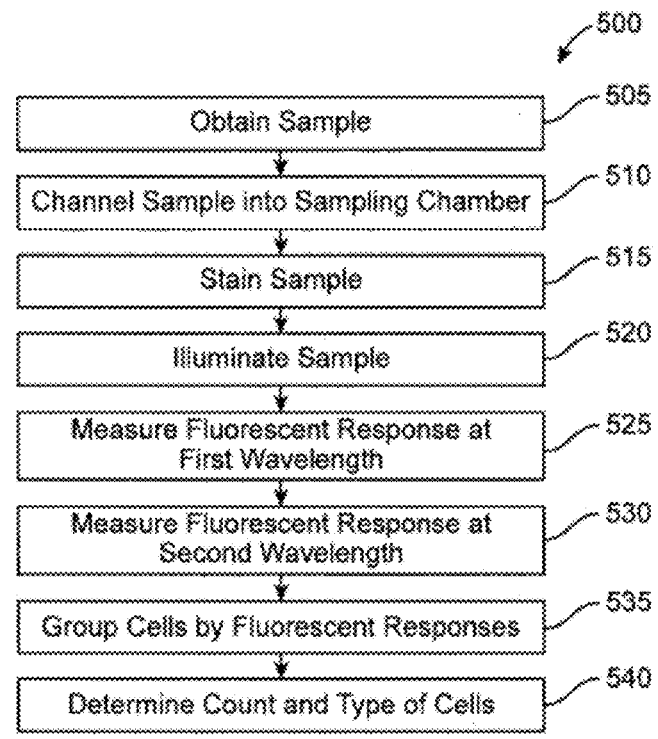
FIG. 5 panel A is a flowchart of a process to count and determine the type of white blood cells in a blood sample. Panel B is a graph illustrating different types of white blood cells in a blood sample based on fluorescence.
Figure 5:
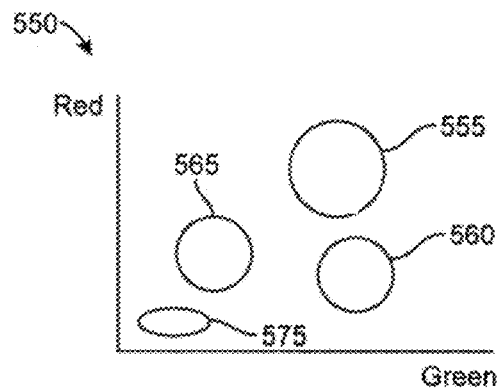

FIG. 5 panel B is a graph illustrating different types of white blood cells in a blood sample that can be identified with a method of the invention based on fluorescence of the white blood cells on an acquired visual data 550. Individual cells, or representations thereof, can be placed on the graph 550 based on the amount of green fluorescent response and red fluorescent response. In the graph 550, the x-axis represents the level of green fluorescent response and the y-axis represents the level of red fluorescent response. The cells placed on the graph 550 can be divided into a plurality of distinct groups based on their fluorescence. For example, the first group 555 can correspond to the number of neutrophils, the second group 560 can correspond to the number of lymphocytes, and the third group 565 can correspond to the number of monocytes, and a fourth group 570 can correspond the number of platelets.

Figure 6:
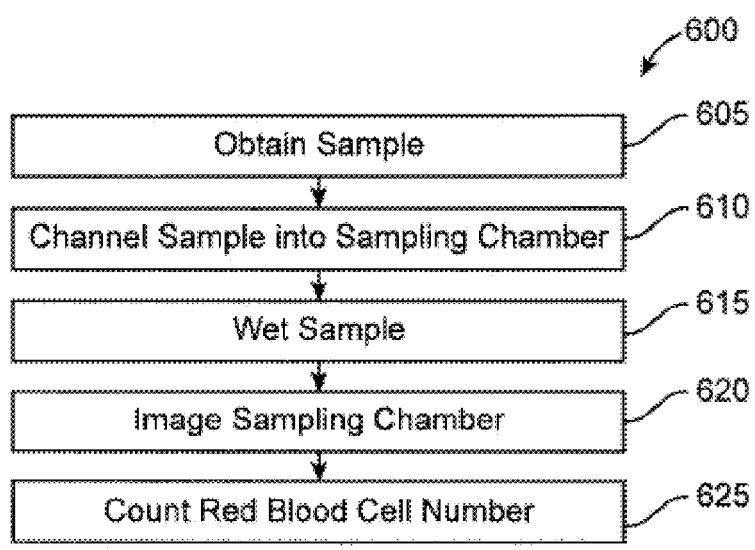
FIG. 6 is a flowchart of a process to count the number of red blood cells in a blood sample.

FIG. 6 is a flowchart of a process 600 illustrating a method to count the number of red blood cells in a blood sample. In 605, a subject provides a small volume of blood sample to a chamber. A subject can use a finger-prick needle to penetrate the skin and to retrieve a drop of blood. A relatively small volume of blood is required, and a drop of blood can be, for example, a sub-microliter volume of blood or a volume of blood between about 1 µL, and about 5 µL. The subject can add the drop of the blood to a chamber, such as the chambers described herein.

In 610, at least a portion of the sample can be channeled into a red blood cell sampling chamber, for example, a first sampling chamber described in 115. In 615 a reagent, such as a surfactant, can be used to sphere red blood cells in the blood sample. After reacting with a surfactant, the red blood cells in the sampling chamber lose their normal bi-concave, disk like shape, and adopt a round, spherical shape. In 620, an imaging system configured to acquire visual data from the slide is taken from the sampling chamber. The chamber can be imaged at one or more wavelengths or wavelength ranges, depending on the type of measurement desired. The rounded red blood cells at the bottom surface of the sampling chamber can be readily identified by their shape, for example, via template matching. At an appropriate dilution, visual data acquired in 620 can comprise a visual representation of more than 100,000 spherical red blood cells at an appropriate dilution. In 625, the number of red blood cells identified in the visual data can be counted to determine red blood cell count (RBC).

Example 2: Systems of the Invention

A system of the invention can comprise a plurality of imaging systems, configured in distinct manners to acquire visual data from a device of the invention.

Figure 7:
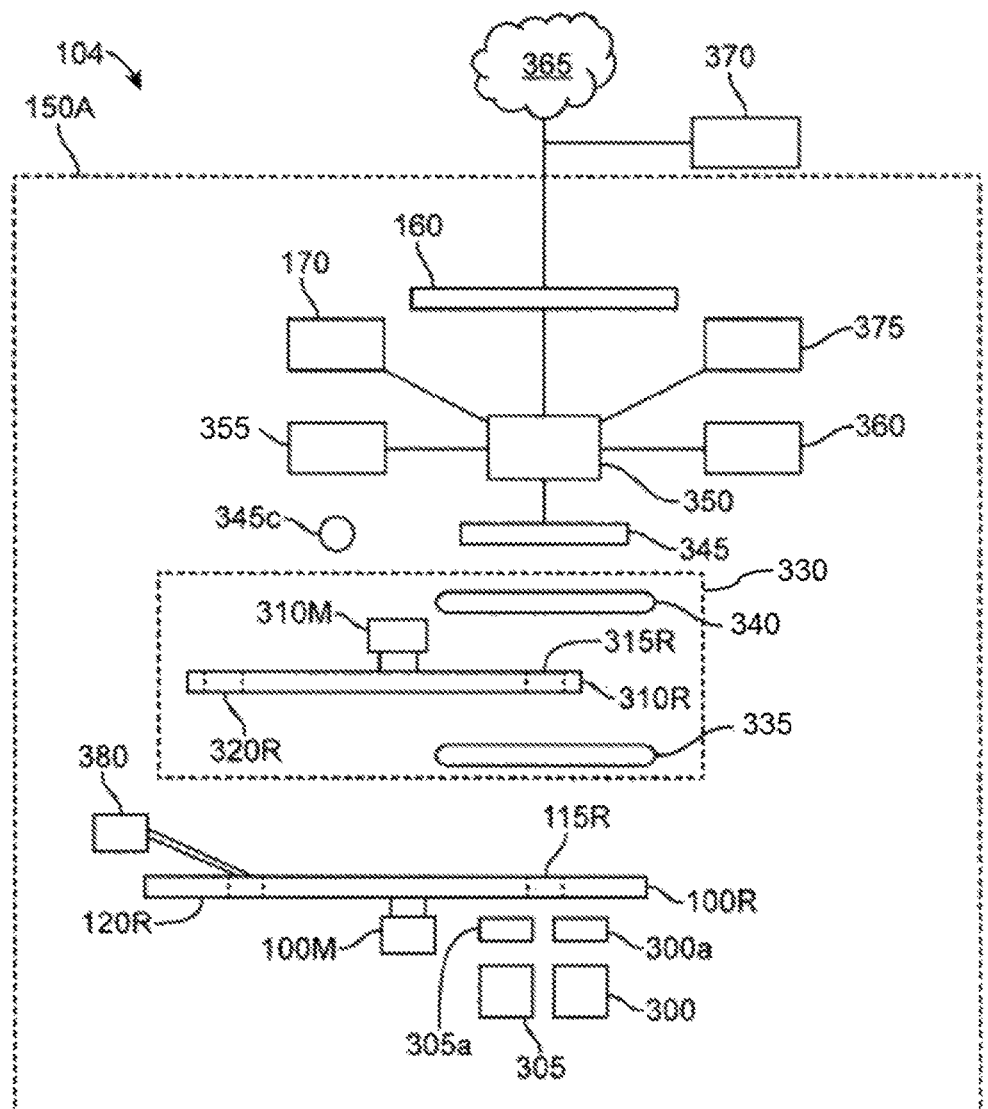
FIG. 7 shows a block diagram of a system and device for analyzing a body fluid.

FIG. 7 shows a block diagram of a system 104 and device for analyzing a body fluid. System 104, particularly the automated portable slide analyzer 150A, can be similar to the system 10 and the automated portable slide analyzer 150, described with reference to FIG. 3. However, this example illustrates a system 104 wherein the blood collection and analysis slide 100R moves via rotation instead of translation to allow an imaging system to capture visual data from different locations within a chamber or within distinct chambers.

The system 104 comprises a motor 100M configured to couple slide 100R and rotate slide 100R for visualizing a desired sampling chamber of the slide 100R. As shown in FIG. 7, the motor 100M can align the sampling chamber 115R of the slide 100R with the light sources 300, 305, as well as the optics assembly 330.

Under instructions from the processor 350, the motor 100M can rotate the slide 100R so that the sampling chamber 120R can be instead aligned with these components so that the sampling chamber 120R can be analyzed instead. The motor 100M can also rotate the slide 100R so that various other features, such as additional chambers or calibration chambers, of the slide 100R can be visualized for analysis.

Other components of the system 104 can be moved by rotation instead of translation. As shown in FIG. 7, for example, system 104 can further comprise a motor 310M coupled to a rotatable filter assembly 310R. Motor 310M can align filter 315R of the filter assembly 310R with the optics assembly 330 and the sampling chamber 115R to be illuminated by the light sources 300 and 305. Under instructions from the processor 350, the motor 310M can rotate the filter assembly 310R so that the filter 320R can instead be aligned with these components. The motor 310M can also rotate the filter assembly 310R so that various other features, such as other filters, of the filter assembly 310R may be aligned with the optical components of the system 104. Both the primary light source 300 and the secondary light source 305 can further comprise condenser optics 300a and 305a, respectively, to facilitate the illumination of the slide and its components, such as by facilitating the formation of a parallel illumination beam. In some embodiments, the automated portable slide analyzer 150A can further comprise an integrated blood collector 380. The integrated blood collector 380 can facilitate collection of the blood sample by subjects and users of the system 104 who are not medically trained collect their own blood.

A system 104 can comprise a first lens 335 and a second lens 340. An image capture element 345 can comprise a CCD or CMOS detector array, for example, a low-cost, high-resolution CCD. The system 104 can further comprise a cooling element 345c for cooling the image capture element 345. A system of the invention can comprise a processor 350, a communications module 360, a transmitter 375, a display 160, and a control panel 170. The processor 350 can be coupled to a transmitter 360 which can transmit 365 acquired visual data to various receivers. A receiver can be coupled with a computer system 370 that is programmed to analyze the visual data.

Figure 8:
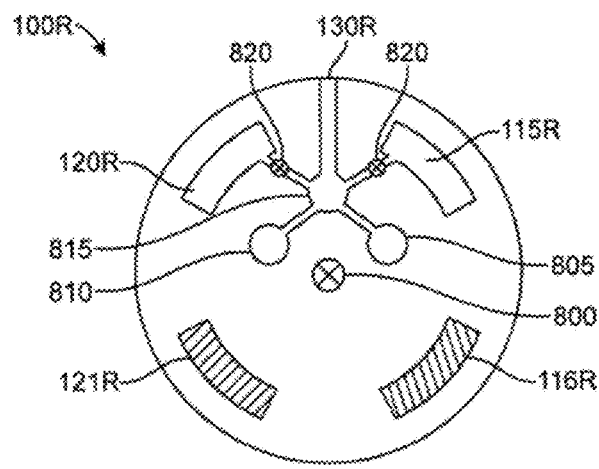
FIG. 8 panel A illustrates the top view of a body fluid collection and analysis slide used. Panel B illustrates a finger rest and body collector. Panel C illustrates a housing comprising an imaging system and a slide/chamber of the invention.
Figure 8:
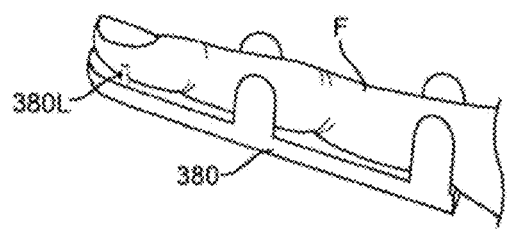
Figure 8:
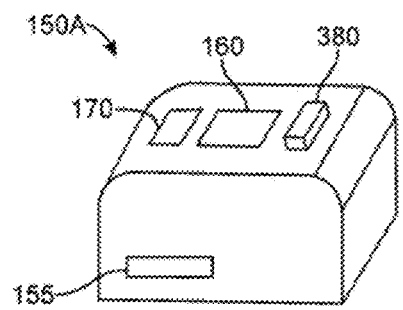

FIG. 8 panel A illustrates the top view of a body fluid collection part and analysis slide described herein. Panel B illustrates a finger rest and body collector. Panel C illustrates a housing comprising an imaging system and a slide/chamber of the invention. As illustrated in panel B, the integrated blood collector 380 can comprise a finger rest having a needle 380L for pricking the subject's finger F and collecting blood therefrom. To avoid contamination, the integrated blood collector 380 can be mounted on the exterior of the automated portable slide analyzer 150A as shown in FIG. 8, panel C (see location of blood collector 380 on slide analyzer 150A). The integrated blood collector 380 can be coupled to the slide 100R shown in Panel A of FIG. 8 to channel collected blood into the slide 100R. Once blood is collected for a round of analysis, the integrated blood collector 380 can be removed from the automated portable slide analyzer 150A and replaced with another integrated blood collector 380.

FIG. 8 shows a top view of a blood collection and analysis slide 100R. The slide 100R comprises a central hub 800 for coupling of the motor 100M to the slide 100R so that the slide 100R can rotate about the central hub 800. The slide 100R can be disposable, be used to collect and analyze blood samples, store various reagents, and generally have many similar functions to the translatable slide 100R described above. Additionally, the motor 100M can rotate the slide 100R to facilitate mixing and to provide for physical separation of various blood components. The motor 100M can also rotate the slide 100R in small and precise increments such that various fields in the focal plane of the sampling chambers 115R and 120R can be imaged sequentially, and in many cases without having to scan the optical components of the system 104, such as the optics assembly 330, the filter assembly 310 or 310R, and the image capture element 345. As discussed above, the images of the various fields can be stitched together digitally to form a large field image of the entire sampling chamber that can be analyzed.

The slide 100R can comprise various components similar to those of the translated slide 100 but adapted for use with a circular, rotated slide 100R. For example, the slide 100R comprises an inlet 130R, a mixing chamber 815, a first reagent storage chamber 805, a second reagent storage chamber 810, valves 820, a first sampling chamber 115R, a second sampling chamber 120R, a first calibration chamber 116R, and a second calibration chamber 121R. The first and second calibration chambers 116R and 121R can be similar to the first and second calibration chambers 116 and 121, respectively, described above and can comprise cell reproductions such as those of white blood cells and red blood cells. The first and second reagent storage chambers 805 and 810 can contain various reagents, for example, one or more of surfactants, dying agents, lysing agents, dry form reagents, liquid reagents, or predetermined volumes of a diluent.

The valves 820 can separate the reagent storage chambers 805 and 810 and the mixing chamber 815 from the first and second sampling chambers 115R and 120R. After blood is collected through inlet 130R, rotation of the slide 100R can generate centrifugal effects that extract the reagents, and diluents in some cases, from the reagent storage chambers 805 and 810 into the mixing chamber 815, where the reagents, blood, and diluents can mix. Centrifugal effects can also be used to separate blood components. The valves 820 can then be opened for this mix to be channeled into the first and second sampling chambers 115R and 120R.

In some embodiments, one or more of the sampling chambers can include various additional reagents. For example, the first sampling chamber 115R can be for analyzing white blood cells and can include a lysing agent to lyse red blood cells to facilitate white blood cell analysis. The valve 820 can prevent the lysing agent from passing from the first sampling chamber 115R into the mixing chamber 815. In addition to channeling of liquids using centrifugal effects, many other ways of manipulating samples can also be used with the rotatable slide 100R, including, for example, the use of suction, microfluidics, pressure mechanisms, capillary action, electrophoresis, and others. Blood samples can also be imaged in many other ways aside from those involving the translation or rotation of a slide.

Example 3: Clinical Applications of a Device, System, and Method of the Invention In order to assess the quality of sample preparation, image acquisition, and image analysis with the devices, systems, and methods of the invention, a study of 13 healthy and unhealthy volunteers was performed, and a comparative analysis between the results obtained with the invention and a commercial automated hematology analyzer was conducted. For each volunteer, blood was drawn once and measured: 1) on a clinical automated hematology analyzer; 2) and using an embodiment of the invention described herein.

Figure 9:
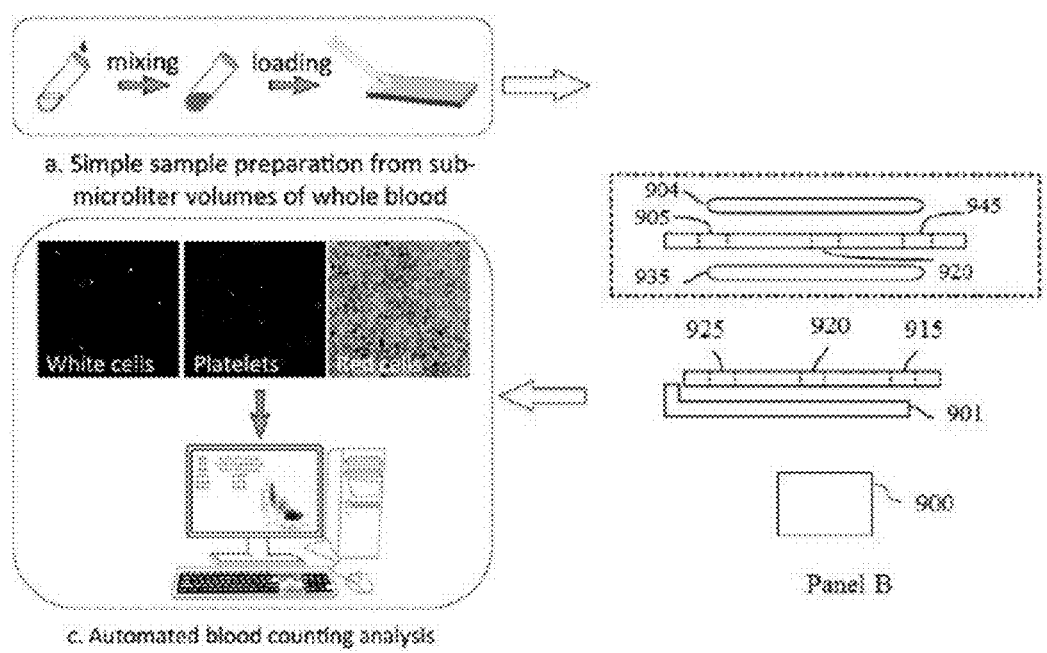
FIG. 9 is a schematic of an automated system for the analysis of a body fluid applied to the analysis of a blood sample. Panel A illustrates a sample preparation. Panel B illustrates an imaging system. Panel C illustrates an automated blood counting analysis.

FIG. 9 is a schematic of a system for the analysis of a body fluid applied to the analysis of a blood sample. Panel A illustrates a sample preparation from sub-microliter volumes of whole-blood. Samples were prepared by diluting sub-microliter volumes of whole blood 20 times in a first reagent, and then injecting the blood sample into a 100-μm-thick chamber of the invention. The first reagent consisted of phosphate buffered saline (pH 7-7.2) with small amounts of the nucleic acid dye acridine orange (AO; 6.25 μM) and the anionic surfactant sodium dodecyl sulfate (SDS; 0.3 mM). The composition of the first reagent maximized the number of parameters that could be extracted from acquired visual images, while minimizing the number of steps in the sample preparation protocol. The use of a first reagent as described herein allowed for the acridine orange to fluorescently stain white blood cells and platelets, while allowing for the red blood cells to become shaped as spheres. The use of a first reagent as described herein also allowed for a uniform monolayer of cells to form at the bottom of a 100 μm thick chamber, the chamber having a surface area of 100 mm$^2$. The protocol was repeated on 3 separate aliquots of each subject's blood. For a single measurement of each subject, visual images were acquired from the same chamber.

FIG. 9 panel B illustrates a compact, low-magnification, wide-field imaging system. Venous blood was drawn from 13 volunteers via venipuncture, and stored in EDTA-treated collection tubes. Samples were immediately run on a Coulter LH500 Hematology™. Following this, sub-microliter aliquots of blood were taken from the tube and diluted between 5 and 20 times in a solution of phosphate buffered saline (PBS) containing 0.1 mM to 0.3 mM sodium dodecyl sulfate (SDS) and 3 μM to 12 μM acridine orange (AO), such that the total volume of the resulting mixture was 10 microliters. The solution was allowed to sit for several minutes to ensure adequate diffusion and staining. The diluted solution was then placed within a commercial 100 micron-thick cell counting chamber with a 10 microliter capacity. Due to the small height of the chamber, the cells were drawn in by capillary forces and formed a uniform layer on the chamber floor.

Automated data analysis techniques were utilized to extract the maximum amount of information from these images in a consistent manner. The visual imaging system utilized a large field of view, and did not require high resolution for the identification of detailed subcellular morphology, since the fluorescent stain allowed separation of white cell types based on chemical rather than morphological differences. Fluorescence intensity in multiple channels was determined for each cell in the image, such that each cell could be represented as a multidimensional point where its position along a given axis represents its intensity in a certain fluorescence channel. For each image, each cell was identified within the visual image by creating a count mask based on a thresholded version of the average of the two fluorescence channels.

A visual image was acquired with the imaging system of panel B, and a transmitter transmitted the acquired visual image to a receiver. Panel C illustrates select steps of the process of visual image data analysis and select components of the visual imaging system. Each cell chamber was placed on the stage of an automated fluorescence microscope 901 (Personal Deltavision™, Applied Precision) and allowed to settle for 5 minutes. For white blood cell measurements, the entire chamber 920 was imaged using a 4×0.13 NA objective 935. Excitation was performed by a Xenon lamp 900 with a 470±20 nm filter 945. Images were acquired using a Photometrics CoolsnapES™ camera attached to the side port of the microscope. Two sequential fluorescence images are acquired for each field of view, one with a green (528±19 nm) 905 filter placed in front of the camera, and second with a red (685±20 nm) 920 filter placed in front of the camera. For platelet images, the objective was changed to a 10×0.25 NA objective 904 and only a portion of the entire chamber 925 was imaged. A single image with the red filter placed in front of the camera was recorded for each field-of-view. Finally, for red cell images, the 915 chamber was imaged, and a 4×0.13 NA objective 935 was used coupled with dark-field illumination from a tungsten bulb passed through a condenser with a ring-mask in the Fourier plane. The illumination contained angles beyond the collection range of the objective. A single color image was recorded using a Nikon D800™ large format camera.

Figure 10:
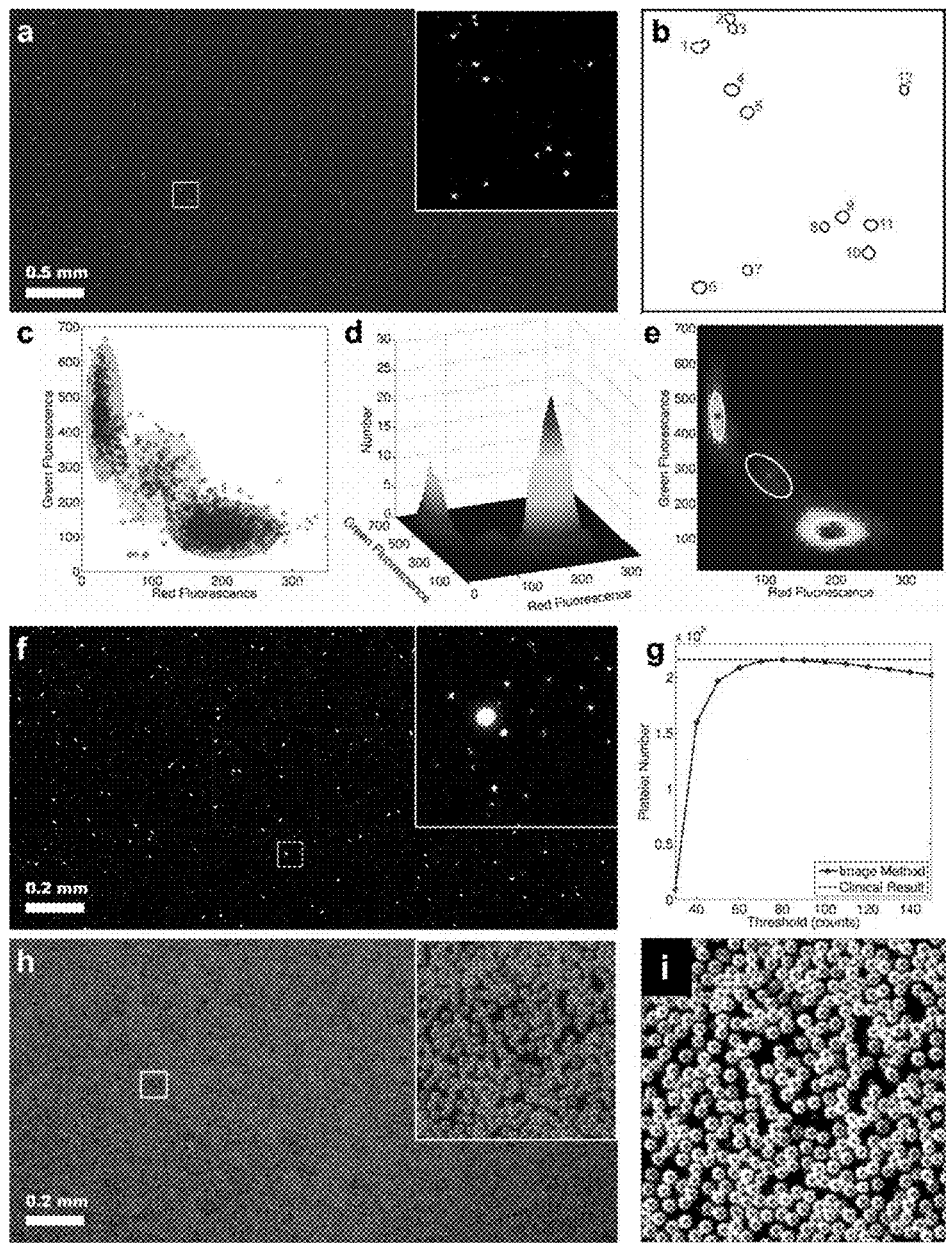
FIG. 10 illustrates visual data acquired with an imaging system. Panel A illustrates merged fluorescent images of white blood cells. Panel B illustrates a count mask formed by thresholding region of interest from Panel A. Panel C is a scatter plot of fluorescent intensities for each object in the white blood cell visual image. Panel D is a histogram of the data in panel C. Panel E is a top down view of panel of Panel D where the surface has been fit with three 2-dimensional Gaussians. Panel F is a visual image illustrating a total-variation denoised fluorescent image used for platelet analysis. Panel G is a graph illustrating the total platelet number as determined from the image in panel F. Panel H is a dark field visual image of red blood cells. Panel I is an overlay of template matching result with inset of panel H.

FIG. 10 illustrates the count mask for the visual image described above. FIG. 10 panel a, panel f, and panel h show the large field-of-view images acquired for white cells, platelets, and red blood cells, respectively. The insets show enlargements of the boxed regions within the larger images. In the white cell images, the cells appear as punctate dots with varying amounts of red and green intensities. Platelets appear as dim objects alongside much larger and brighter white blood cells. Red cells, meanwhile, appear as bright rings. Although the red cells have been sphered, dark field imaging of red cells provided imaging contrast at the membrane. Therefore, the red blood cells appeared as rings rather than opaque disks.

The fluorescence intensity of each white cell was calculated for each channel of the image by finding the mean red or green intensities within each element of the count mask. Plotting the red versus green intensity for all cells in an image yielded plots as shown in FIG. 10, panel C. This image illustrates that the cells clustered into three distinct regions (shaded areas provided as a visual reference). One group of cells was characterized by low red fluorescence and intense green fluorescence, indicating low amounts of RNA, but large and concentrated amounts of DNA in the cells. These are lymphocytes, which, in their resting state, have little active transcription. Another group of cells was characterized by high red fluorescence, and low green fluorescence. This pattern corresponded to granulocytes, which have large amounts of RNA, as well as granules, that stained red with the acridine orange of reagent 1. Another group of cells, the center group in panel c, was characterized by a moderate staining. Those cells were monocytes, and they are characterized by a moderate transcription activity.

To better distinguish between the overlap within the groups, the data was modeled with a Gaussian mixture model. The cell-level data and individual data points were taken into a two-dimensional histogram. That process yielded a 3-dimensional surface, as shown in FIG. 10, panel D. By fitting these peaks in panel d with 2-dimensional Gaussian models, the relative percentage of the total white cell count in each cluster was determined. This model-based approach allowed the underlying distribution of cells in the blood to be accurately estimated, even though the total number of cells measured by the instrument was significantly smaller than the total number of cells required by traditional flow instruments.

FIG. 10 panel e illustrates an overlay of Gaussian fits on the raw data. In this top-down view, the height of the peaks are shown by varying shading levels with height increasing toward the centers of the Gaussian fits. The 1/e contour of each Gaussian is marked with a thick white line.

Platelets are an important parameter to be determined in a complete blood count. When stained with acridine orange, platelet fluorescence is generally dimmer than the fluorescence provided by other cell types, due to the smaller amount of nucleic acid within each platelet. To acquire a visual image that could accurately detect the dimmer fluorescence from the platelets, an objective lens with larger numerical aperture was used to perform these measurements. Because the signal-to-noise ratios of the platelet visual images are relatively low, the visual images were first denoised using a total-variation constrained denoising technique. A denoising algorithm utilized an L1-norm minimization that smoothed out noise while preserving sharp edges within the image, which was necessary for identifying small and dim platelets. After applying the denoising algorithm, the image was binarized by setting a specific threshold value, and the number of platelets was counted using a count mask, in a manner similar as to what was described above for the white cell analysis. The size of each particle was analyzed in the count mask, and objects with very large sizes were discarded filter out white cells (which also fluoresce red) from the platelet count. Because different subjects have different amounts of platelet fluorescence (as fluorescence intensity is strongly correlated with platelet age), it is was not possible to select a single intensity threshold for all subjects. To solve this challenge, for each platelet image the count was performed at a wide range of thresholds. This generated a count-versus-threshold curve, as shown in FIG. 10 panel g. The maximum value along this curve, eliminated contributions from noise pixels, and at the same time avoided missing platelets with weakest fluorescence.

The fluorescence intensity was also calculated for a red blood cell population. Each red blood cell in each image was identified by template matching. Several template images were created, each template consisting of a single red blood cell on a black background. Since the red blood cells were uniform in shape after being treated with sodium dodecyl sulfate, it was sufficient to use 3 templates of cells of slightly different sizes to characterize a red blood cell population. After the red blood cell visual image was cropped to remove regions from the edge of the field of view (where field dependent aberrations can become significant or where only a portion of the cell is visible), a normalized cross correlation was computed between each template and the visual image. When the cells in a template cells were similar to the cells in the visual image, the cross correlation between images consisted of several sharp peaks at the locations of cells within the image.

To identify and count each cell, regions of the cross correlation map that were higher than their local neighborhood were defined using the extended-maxima transform (MATLAB function imextendedmax). For each template, a binary image was created wherein regions of extended maxima in the cross-correlation were defined as one and all other portions of the image were defined as zero. All binary images from all templates were combined using an "or" criterion. However, while this analysis accurately identified nearly all cells in the image, it could also identify regions of the background that have larger correlation values than their neighbors. To separate these background regions from correctly counted regions, a count mask was created based on the combined binary extended maxima maps. For each component of this mask, both the average value of the original image, and the average value of the cross correlation map were found. True cells were expected to have either high image intensity, or high correlation values, while background counts were expected to be low on both of these axes. Therefore, a threshold image intensity and threshold correlation value were set, segmenting the space into 4 quadrants. All counts in the lower left quadrant were then excluded. An overlay of the final intensity-and-correlation-filtered a binary image, which had a "dot" at the location of each cell in the image, and the original dark field image is shown in FIG. 10 panel i.

Following data acquisition, the images were submitted to automated routines to enumerate and differentiate cells. All processing was done with MATLAB (The MathWorks, Natick, Mass.) using custom scripts developed in-house. In order to determine volumes represented by each image, the exact magnification of the imaging system was calibrated using a USAF1951 resolution target. This, combined with the known height of the cell counting chambers, allowed computation of the volume of sample measured by each image.

Figure 11:
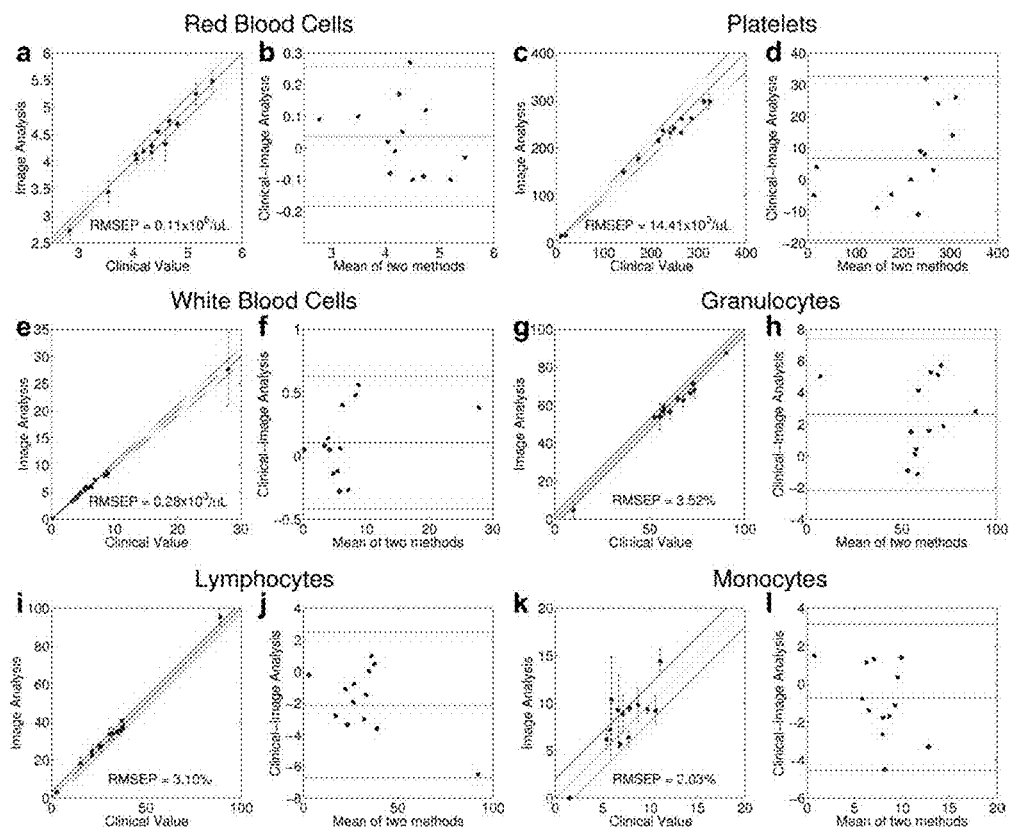
FIG. 11 illustrates a comparison of image-based determination of CBC parameters with clinical results from an automated hematology analyzer. Panel A is a graph illustrating a visual image analysis versus clinical value for red blood cells. Panel B is a graph illustrating the difference between the two methods plotted against their mean for red blood cells. Panel C is a graph illustrating a visual image analysis versus clinical value for platelets. Panel D is a graph illustrating the difference between the two methods plotted against their mean for platelets. Panel E is a graph illustrating a visual image analysis versus clinical value for white blood cells. Panel F is a graph illustrating the difference between the two methods plotted against their mean for white blood cells. Panel G is a graph illustrating a visual image analysis versus clinical value for granulocytes. Panel H is a graph illustrating the difference between the two methods plotted against their mean for granulocytes. Panel I is a graph illustrating a visual image analysis versus clinical value for Lymphocytes. Panel J is a graph illustrating the difference between the two methods plotted against their mean for Lymphocytes. Panel K is a graph illustrating a visual image analysis versus clinical value for Monocytes. Panel L is a graph illustrating the difference between the two methods plotted against their mean for Monocytes.

FIG. 11 illustrates a comparison of image-based determination of CBC parameters obtained with a method of the invention to clinical results obtained from an automated hematology analyzer. For each component of the complete blood count, FIG. 11 shows a correlation between a result obtained with a method described herein and a clinical result. FIG. 11 also illustrates a Tukey mean-difference plot for the results obtained with a method described herein and the results obtained with an automated clinical instrument. For the correlation plots (FIG. 11 panel a, panel c, panel e, panel g, panel i, and panel k), the x-axis represents the value reported by the clinical instrument, while the y-axis represents the value predicted by the method. The middle diagonal line in each figure represents the line of perfect agreement between the two methods. The lines above and below the middle line represent the error range of the clinical measurement, defined as ±2 standard deviations, as reported by the manufacturer. For each blood count parameter, the root-mean-squared error in prediction (RMSEP), a measure of the average error between the measurements, was calculated. RMSEP is defined as:

$$RMSEP = \mathrm{sqrt}(\mathrm{sum}\ i=1\char`\^ N(Ci-M1)\char`\^ 2);$$

wherein N is the number of patients, C, is the clinical value for the $i^{th}$ patient, and M, is the prediction from the method for that patient. These errors are presented in TABLE 1.

TABLE 1

| | |
|---|---|
| Red Blood Cell | $0.12 \times 10^6$ cells/μL |
| Platelet | $16.8 \times 10^3$ platelets/μL |

TABLE 1-continued

| | |
|---|---|
| White Blood Cell | $0.03 \times 10^3$ cells/μL |
| Granulocyte | 3.38% |
| Lymphocyte | 2.19% |
| Monocyte | 2.20% |

For all parameters except the monocyte differential, the clinical measurement and the method produced results that agree within the margin of error of the clinical instrument. As illustrated in FIG. 11 panel e, monocytes and granulocytes overlap slightly, with the degree of overlap varying slightly from subject to subject. This overlap can lead to errors in the Gaussian mixture modeling of the data. In some cases, a systematic error in modeling that could lead to overcounting the number of monocytes and undercounting the number of granulocytes was observed.

To further assess the degree to which the results obtained with the invention are compatible with the results obtained with standard clinical measurements, Tukey mean-difference plots were created, and are illustrated in FIG. 11 panel b, panel d, panel f, panel h, panel j, and panel l. In these plots, the x-axis represents the mean of the clinical and image-based measurements, while the y-axis represents the difference between these two measurements. The average difference across all samples is shown in red, and the ±1.96 standard deviation lines (representing the 95% confidence intervals) are shown in green, representing the maximum expected disagreement between the two methods. The observed maximum deviation from the clinical measurement for each count group was low, especially when compared to clinically significant fluctuations in complete blood cell counts.

Example 4: Computer Architectures for the Analysis of a Visual Image

Figure 12:
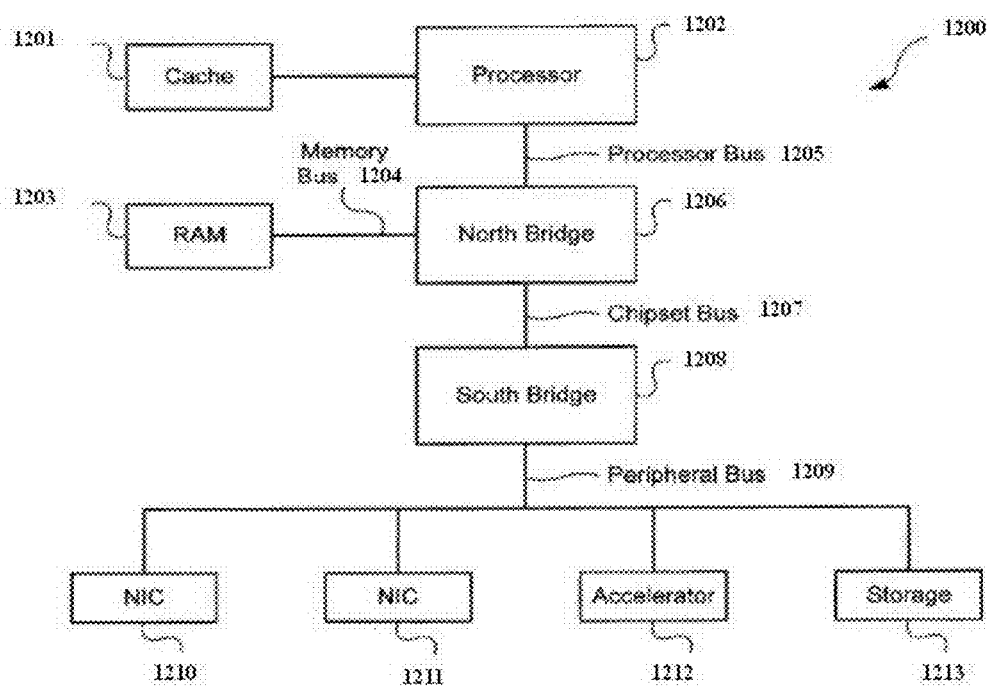
FIG. 12 is a block diagram illustrating a first example architecture of a computer system that can be used in connection with example embodiments of the present invention.

Sequencing data can be analyzed by a plurality of computers, with various computer architectures. Various computer architectures are suitable for use with the invention. FIG. 12 is a block diagram illustrating a first example architecture of a computer system 1200 that can be used in connection with example embodiments of the present invention. As depicted in FIG. 12, the example computer system can include a processor 1202 for processing instructions. Non-limiting examples of processors include: Intel Core i7™ processor, Intel Core i5™ processor, Intel Core i3™ processor, Intel Xeon™ processor, AMD Opteron™ processor, Samsung 32-bit RISC ARM 1176JZ(F)-S v1.0™ processor, ARM Cortex-A8 Samsung SSPC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can be used, whether in a single computer system, in a cluster, or distributed across systems over a network comprising a plurality of computers, cell phones, and/or personal data assistant devices.

As illustrated in FIG. 12, a high speed cache 1201 can be connected to, or incorporated in, the processor 1202 to provide a high speed memory for instructions or data that have been recently, or are frequently, used by processor 1202. The processor 1202 is connected to a north bridge 1206 by a processor bus 1205. The north bridge 1206 is connected to random access memory (RAM) 1203 by a memory bus 1204 and manages access to the RAM 1203 by the processor 1202. The north bridge 1206 is also connected to a south bridge 1208 by a chipset bus 1207. The south bridge 1208 is, in turn, connected to a peripheral bus 1209. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 1209. In some architectures, the functionality of the north bridge can be incorporated into the processor instead of using a separate north bridge chip.

In some embodiments, system 1200 can include an accelerator card 1212 attached to the peripheral bus 1209. The accelerator can include field programmable gate arrays (FPGAs) or other hardware for accelerating certain processing.

Software and data are stored in external storage 1213 and can be loaded into RAM 1203 and/or cache 1201 for use by the processor. The system 1200 includes an operating system for managing system resources; non-limiting examples of operating systems include: Linux, Windows™, MACOS™, BlackBerry OS™, iOS™, and other functionally-equivalent operating systems, as well as application software running on top of the operating system.

In this example, system 1200 also includes network interface cards (NICs) 1210 and 1211 connected to the peripheral bus for providing network interfaces to external storage, such as Network Attached Storage (NAS) and other computer systems that can be used for distributed parallel processing.

Figure 13:
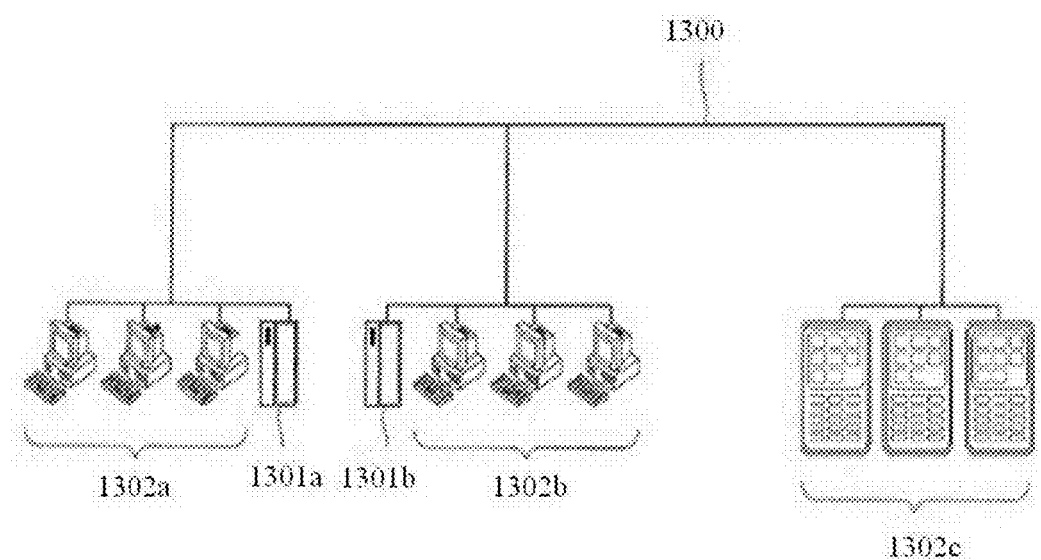
FIG. 13 is a diagram illustrating a computer network that can be used in connection with example embodiments of the present invention.

FIG. 13 is a diagram showing a network 1300 with a plurality of computer systems 1302*a*, and 1302*b*, a plurality of cell phones and personal data assistants 1302*c*, and Network Attached Storage (NAS) 1301*a*, and 1301*b*. In some embodiments, systems 1302*a*, 1302*b*, and 1302*c* can manage data storage and optimize data access for data stored in Network Attached Storage (NAS) 1301*a* and 1302*b*. A mathematical model can be used for the data and be evaluated using distributed parallel processing across computer systems 1302*a*, and 1302*b*, and cell phone and personal data assistant systems 1302*c*. Computer systems 1302*a*, and 1302*b*, and cell phone and personal data assistant systems 1302*c* can also provide parallel processing for adaptive data restructuring of the data stored in Network Attached Storage (NAS) 1301*a* and 1301*b*. FIG. 13 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface. In some embodiments, processors can maintain separate memory spaces and transmit data through network interfaces, back plane, or other connectors for parallel processing by other processors. In some embodiments, some or all of the processors can use a shared virtual address memory space.

Figure 14:
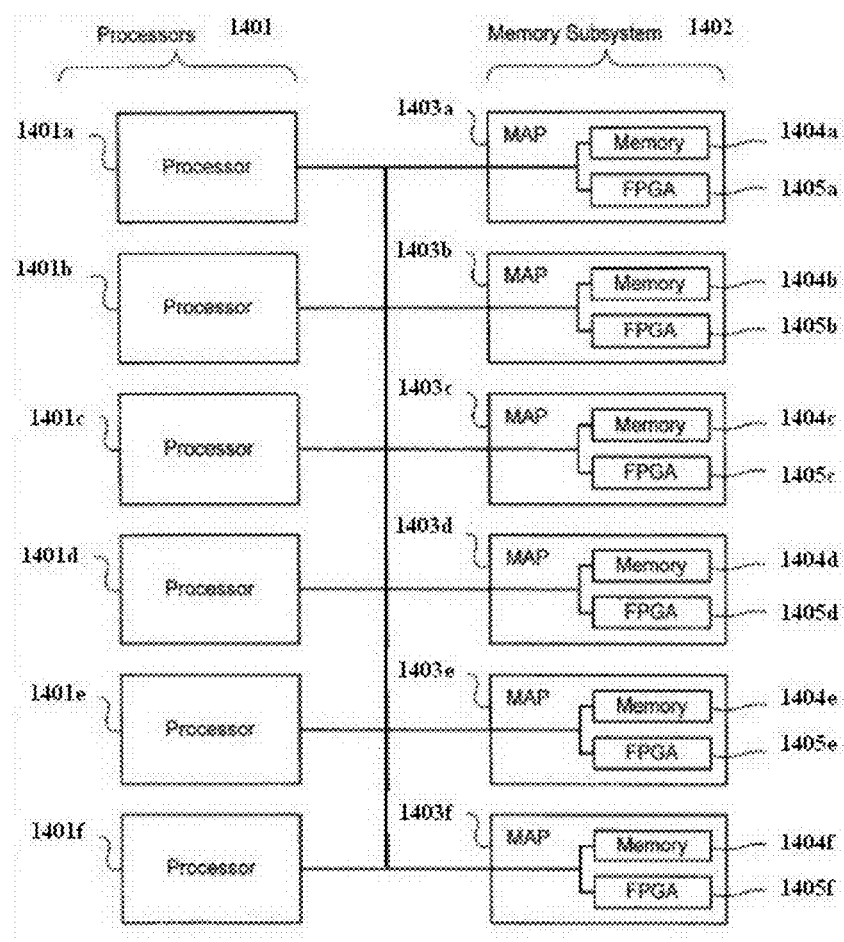
FIG. 14 is a block diagram illustrating a second example architecture of a computer system that can be used in connection with example embodiments of the present invention.

FIG. 14 is a block diagram of a multiprocessor computer system using a shared virtual address memory space. The system includes a plurality of processors 1401*a-f* that can access a shared memory subsystem 1402. The system incorporates a plurality of programmable hardware memory algorithm processors (MAPs) 1403*a-f* in the memory subsystem 1402. Each MAP 1403*a-f* can comprise a memory 1404*a-f* and one or more field programmable gate arrays (FPGAs) 1405*a-f*. The MAP provides a configurable functional unit and particular algorithms or portions of algorithms can be provided to the FPGAs 1405*a-f* for processing in close coordination with a respective processor. In this example, each MAP is globally accessible by all of the processors for these purposes. In one configuration, each MAP can use Direct Memory Access (DMA) to access an associated memory 1404*a-f*, allowing it to execute tasks independently of, and asynchronously from, the respective microprocessor 1401*a-f*. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 14, system on chips (SOCs), application specific integrated circuits (ASICs), or other processing and logic elements. For example, the Set Processor and Optimizer can be implemented with hardware acceleration through the use of a hardware accelerator card, such as accelerator card 1212 illustrated in FIG. 12.

EMBODIMENTS

The following non-limiting embodiments provide illustrative examples of the invention, but do not limit the scope of the invention.

Embodiment 1

In some embodiments, the invention provides a device comprising: a) a slide configured to receive a body fluid, wherein the slide comprises: i) a first chamber, wherein the first chamber contains a first reagent capable of detecting a first analyte in the body fluid; and ii) a second chamber, wherein the second chamber contains a second reagent capable of detecting a second analyte in the body fluid; and b) an imaging system configured to acquire visual data from the slide.

Embodiment 2

The device of embodiment 1, further comprising a transmitter, wherein the transmitter is configured to transmit the acquired visual data to a receiver.

Embodiment 3

The device of embodiment 2, wherein the transmission is wireless.

Embodiment 4

The device of any one of embodiments 1-3, wherein the body fluid is urine.

Embodiment 5

The device of any one of embodiments 1-4, wherein the body fluid is blood.

Embodiment 6

The device of any one of embodiments 1-5, wherein the first analyte is a red blood cell.

Embodiment 7

The device of embodiment 6, wherein the second analyte is a white blood cell.

Embodiment 8

The device of any one of embodiments 1-7, wherein the slide and the imaging system are contained in a common housing.

Embodiment 9

The device of embodiment 8, wherein the slide is removable.

Embodiment 10

The device of any one of embodiments 1-9, wherein the slide further comprises a channel across a surface of the slide, wherein the channel is in connection with the first chamber and the second chamber.

Embodiment 11

The device of embodiment 10, wherein the slide further comprises a port, wherein the port is configured to receive the body fluid and pass the body fluid through the channel to at least one chamber.

Embodiment 12

The device of any one of embodiments 1-11, wherein the slide further comprises a third chamber, wherein the third chamber contains a third reagent capable of detecting a third analyte in the body fluid.

Embodiment 13

The device of embodiment 12, wherein the third analyte is a platelet.

Embodiment 14

The device of any one of embodiments 1-13, wherein the slide further comprises at least one control chamber, wherein the control chamber contains a control analyte.

Embodiment 15

The device of any one of embodiments 1-14, wherein the slide is holds no greater than 5 microliters of body fluid.

Embodiment 16

In some embodiments, the invention provides a device comprising: a) a slide configured to receive a body fluid; b) an imaging system configured to acquire visual data from the slide; and c) a transmitter configured to wirelessly-transmit the acquired visual data over a distance of at least one mile.

Embodiment 17

The device of embodiment 16, wherein the device has a mass of no greater than 2,000 g.

Embodiment 18

The device of any one of embodiments 16-17, wherein the imaging system acquires visual data from at least two different parts of the slide.

Embodiment 19

The device of any one of embodiments 16-18, wherein the slide and the imaging system are contained in a common housing.

Embodiment 20

The device of embodiment 19, wherein the slide is removable.

Embodiment 21

The device of any one of embodiments 16-20, wherein the body fluid is saliva.

Embodiment 22

The device of any one of embodiments 16-21, wherein the body fluid is blood.

Embodiment 23

The device of any one of embodiments 16-22, wherein the imaging system is configured to detect an analyte in the body fluid.

Embodiment 24

The device of embodiment 23, wherein the analyte is a red blood cell.

Embodiment 25

The device of embodiment 23, wherein the analyte is a white blood cell.

Embodiment 26

The device of embodiment 23, wherein the analyte is a platelet.

Embodiment 27

The device of any one of embodiments 16-26, wherein the slide holds no greater than 5 microliters of body fluid.

Embodiment 28

In some embodiments, the invention provides a method for analyzing a body fluid, the method comprising: a)

providing the body fluid to a slide, wherein the slide comprises a first chamber and a second chamber; b) detecting in the first chamber a first analyte in the body fluid with a first reagent; c) detecting in the second chamber a second analyte in the body fluid with a second reagent; d) acquiring by an imaging system visual data from the slide; and e) transmitting the acquired visual data to a receiver by a transmitter.

Embodiment 29

The method of embodiment 28, wherein from about 1 microliter to about 5 microliters of body fluid is provided to the slide.

Embodiment 30

The method of any one of embodiments 28-29, wherein the transmission is wireless.

Embodiment 31

The method of embodiment 30, wherein the transmitter and the receiver are at least one mile apart.

Embodiment 32

The method of any one of embodiments 28-31, wherein the body fluid is saliva.

Embodiment 33

The method of any one of embodiments 28-31, wherein the body fluid is blood.

Embodiment 34

The method of any one of embodiments 28-31, wherein the first analyte is a red blood cell.

Embodiment 35

The method of embodiment 34, wherein the second analyte is a white blood cell.

Embodiment 36

The method of embodiment 35, wherein the slide further comprises a third chamber, wherein the method further comprises detecting in the third chamber a third analyte in the body fluid with a third reagent.

Embodiment 37

The method of embodiment 36, wherein the third analyte is a platelet.

Embodiment 38

The method of any one of embodiments 28-37, wherein the slide further comprises a channel across the surface of the slide, wherein the channel is in connection with the first chamber and the second chamber.

Embodiment 39

The method of any one of embodiments 28-38, wherein the device further comprises a port, wherein the port is configured to receive the body fluid and pass the body fluid through the channel to at least one chamber.

Embodiment 40

The method of any one of embodiments 28-39, further comprising converting the acquired visual data to an image.

Embodiment 41

In some embodiments, the invention provides a system comprising: a) a device comprising: i) a slide configured to receive a body fluid; ii) an imaging system configured to acquire visual data from the slide; and iii) a transmitter, wherein the transmitter wirelessly transmits the acquired visual data; and b) a receiver that receives the wirelessly-transmitted visual data from the transmitter, wherein the transmitter and the receiver are configured to communicate over a distance of at least 1 mile.

Embodiment 42

The system of embodiment 41, wherein the device has a mass of no greater than 2,000 g.

Embodiment 43

The system of any one of embodiments 41-42, wherein the imaging system is configured to acquire visual data from at least two different parts of the slide.

Embodiment 44

The system of any one of embodiments 41-43, wherein the slide, the imaging system, and the transmitter are contained in a common housing.

Embodiment 45

The system of any one of embodiments 41-44, wherein the body fluid is saliva.

Embodiment 46

The system of any one of embodiments 41-44, wherein the body fluid is blood.

Embodiment 47

The system of any one of embodiments 41-46, wherein the slide comprises at least two chambers.

Embodiment 48

The system of any one of embodiments 41-47, wherein the slide further comprises a channel across the surface of the slide, wherein the channel is in connection with a first chamber and a second chamber.

Embodiment 49

The system of any one of embodiments 41-48, wherein the imaging system is configured to detect an analyte in the body fluid.

Embodiment 50

The system of embodiment 49, wherein the analyte is a red blood cell.

Embodiment 51

The system of embodiment 49, wherein the analyte is a white blood cell.

Embodiment 52

The system of embodiment 49, wherein the analyte is a platelet.

Embodiment 53

The system of any one of embodiments 41-52, wherein the slide holds no greater than 5 microliters of body fluid.

Embodiment 54

The system of any one of embodiments 41-53, wherein the receiver is in communication with a computer system configured to generate an image based on the acquired visual data.

Embodiment 55

A kit comprising: a) a device comprising: i) a slide configured to receive a body fluid, wherein the slide comprises a first chamber and a second chamber; and ii) an imaging system configured to acquire visual data from the slide; b) a first reagent capable of detecting a first cell type in the body fluid; and c) a second reagent capable of detecting a second cell type in the body fluid.

Embodiment 56

The kit of embodiment 55, wherein the slide further comprises a channel across the surface of the slide, wherein the channel is in connection with the first chamber and the second chamber.

Embodiment 57

The kit of any one of embodiments 55-56, wherein the slide further comprises a port, wherein the port is configured to receive the body fluid and pass the body fluid through the channel to at least one chamber.

Embodiment 58

The kit of any one of embodiments 55-57, wherein the first cell type is a red blood cell.

Embodiment 59

The kit of embodiment 58, wherein the second cell type is a white blood cell.

Embodiment 60

The kit of embodiment 59, wherein the slide further comprises a third chamber, wherein the kit comprises a third reagent capable of detecting a third cell type in the body fluid.

Embodiment 61

The kit of embodiment 60, wherein the third cell type is a platelet.

What is claimed is:

1. A device comprising:
    a) a slide configured to receive a body fluid, wherein the slide comprises:
        i) a first chamber, wherein the first chamber contains a first reagent that detects a red blood cell in the body fluid by sphering the red blood cell; and
        ii) a second chamber, wherein the second chamber contains a second reagent that differentiates a white blood cell in the body fluid from the red blood cell, wherein the first chamber and the second chamber are connected by a fluidic channel; and
    b) an imaging system that acquires an image of the red blood cell from the first chamber and an image of the white blood cell from the second chamber of the slide.

2. The device of claim 1, further comprising a transmitter, wherein the transmitter is configured to transmit the image of the red blood cell and the image of the white blood cell to a receiver.

3. The device of claim 2, wherein the transmission is wireless.

4. The device of claim 2, wherein the transmission and the receiver are at least one mile apart.

5. The device of claim 1, wherein the body fluid is urine.

6. The device of claim 1, wherein the body fluid is blood.

7. The device of claim 1, wherein the slide and the imaging system are contained in a common housing.

8. The device of claim 7, wherein the slide is removable.

9. The device of claim 1, wherein the fluidic channel is across a surface of the slide.

10. The device of claim 1, wherein the slide further comprises a port, wherein the port is configured to receive the body fluid and pass the body fluid through the fluidic channel to the first chamber or the second chamber.

11. The device of claim 1, wherein the slide further comprises a third chamber, wherein the third chamber contains a third reagent that stains a platelet in the body fluid.

12. The device of claim 1, wherein the slide is configured to receive from about 1 microliter to about 5 microliters of the body fluid.

13. The device of claim 1, wherein the body fluid is saliva.

14. The device of claim 1, wherein the slide further comprises at least one control chamber, wherein the control chamber contains a control analyte.

15. The device of claim 1, wherein the second reagent stains the white blood cell.

16. The device of claim 1, wherein the device has a mass of no greater than 2,000 g, wherein the device has a minimum total mass of about 100 g.

17. A device comprising:
    a) a slide configured to receive a body fluid, wherein the slide comprises a first chamber and a second chamber, wherein the first chamber contains a first reagent that spheres a red blood cell in the body fluid, and the second chamber contains a second reagent that differentiates a white blood cell in the body fluid from the red blood cell;
    b) an imaging system that acquires an image of the red blood cell from the first chamber and an image of the white blood cell from the second chamber of the slide; and c) a transmitter configured to wirelessly-transmit the image of the red blood cell from the first chamber and the image of the white blood cell from the second chamber of the slide over a distance of at least one mile.

18. The device of claim 17, wherein the device has a mass of no greater than 2,000 g, wherein the device has a minimum total mass of about 100 g.

19. The device of claim 17, wherein the slide and the imaging system are contained in a common housing.

20. The device of claim 19, wherein the slide is removable.

21. The device of claim 17, wherein the body fluid is saliva.

22. The device of claim 17, wherein the body fluid is blood.

23. The device of claim 17, wherein the slide further comprises a third chamber, wherein the third chamber contains a third reagent that stains a platelet in the body fluid.

24. The device of claim 17, wherein the slide is configured to receive from about 1 microliter to about 5 microliters of the body fluid.

25. The device of claim 17, wherein the body fluid is urine.

26. The device of claim 17, wherein the slide further comprises a port, wherein the port is configured to receive the body fluid and pass the body fluid through a fluidic channel to the first chamber or the second chamber.

27. The device of claim 17, wherein the slide further comprises at least one control chamber, wherein the control chamber contains a control analyte.

28. The device of claim 17, wherein a fluidic channel is across a surface of the slide.

29. The device of claim 17, wherein the second reagent stains the white blood cell.

30. A method for analyzing a body fluid, the method comprising:
   a) providing the body fluid to a slide, wherein the slide comprises a first chamber and a second chamber, wherein the first chamber and the second chamber are connected by a fluidic channel;
   b) detecting in the first chamber a red blood cell in the body fluid with a first reagent that spheres the red blood cell;
   c) detecting in the second chamber a white blood cell in the body fluid with a second reagent that differentiates the white blood cell in the body fluid from the red blood cell; and
   d) acquiring by an imaging system an image of the red blood cell from the first chamber and an image of the white blood cell from the second chamber of the slide.

31. The method of claim 30, wherein the slide is configured to receive from about 1 microliter to about 5 microliters of the body fluid.

32. The method of claim 30, wherein the body fluid is saliva.

33. The method of claim 30, wherein the body fluid is blood.

34. The method of claim 30, wherein the slide further comprises a third chamber, wherein the method further comprises staining in the third chamber a platelet in the body fluid with a third reagent.

35. The method of claim 30, wherein the fluidic channel is across a surface of the slide.

36. The method of claim 30, wherein the device further comprises a port, wherein the port is configured to receive the body fluid and pass the body fluid through the fluidic channel to the first chamber or the second chamber.

37. The method of claim 30, further comprising transmitting the image of the red blood cell from the first chamber and the image of the white blood cell from the second chamber to a receiver by a transmitter.

38. The method of claim 37, wherein the transmission is wireless.

39. The method of claim 37, wherein the transmitter and the receiver are at least one mile apart.

40. A system comprising:
   a) a device comprising:
      i) a slide configured to receive a body fluid, wherein the slide comprises a first chamber that contains a first reagent that spheres a red blood cell and a second chamber that contains a second reagent that differentiates a white blood cell in the body fluid from the red blood cell, wherein the first chamber and the second chamber are connected by a fluidic channel;
      ii) an imaging system that acquires an image of the red blood cell from the first chamber and an image of the white blood cell from the second chamber of the slide; and
      iii) a transmitter, wherein the transmitter wirelessly transmits the image from the first chamber and the image from the second chamber; and
   b) a receiver that receives the wirelessly-transmitted image from the first chamber and the wirelessly-transmitted image from the second chamber from the transmitter, wherein the transmitter and the receiver are configured to communicate over a distance of at least 1 mile.

41. The system of claim 40, wherein the device has a mass of no greater than 2,000 g, wherein the device has a minimum total mass of about 100 g.

42. The system of claim 40, wherein the slide, the imaging system, and the transmitter are contained in a common housing.

43. The system of claim 40, wherein the body fluid is saliva.

44. The system of claim 40, wherein the body fluid is blood.

45. The system of claim 40, wherein the slide further comprises a third chamber, wherein the third chamber contains a third reagent that stains a platelet in the body fluid.

46. The system of claim 40, wherein the slide is configured to receive from about 1 microliter to about 5 microliters of the body fluid.

47. The system of claim 40, wherein the slide further comprises a port, wherein the port is configured to receive the body fluid and pass the body fluid through the fluidic channel to the first chamber or the second chamber.

48. The system of claim 40, wherein the slide further comprises at least one control chamber, wherein the control chamber contains a control analyte.

49. The system of claim 40, wherein the slide and the imaging system are contained in a common housing.

50. The system of claim 40, wherein the body fluid is urine.

51. A kit comprising:
   a) a device comprising:
      i) a slide configured to receive a body fluid, wherein the slide comprises a first chamber and a second chamber, wherein the first chamber and the second chamber are connected by a fluidic channel; and ii) an imaging system that acquires an image of a red blood cell from the first chamber and an image of a white blood cell from the second chamber of the slide;
b) a first reagent that spheres the red blood cell in the body fluid in the first chamber; and
c) a second reagent that differentiates the white blood cell in the body fluid from the red blood cell in the second chamber.

52. The kit of claim 51, wherein the slide further comprises a port, wherein the port is configured to receive the body fluid and pass the body fluid through the fluidic channel to the first chamber or the second chamber.

53. The kit of claim 51, wherein the slide further comprises a third chamber, wherein the third chamber comprises a third reagent that stains a platelet in the body fluid.

54. The kit of claim 51, wherein the slide is configured to receive from about 1 microliter to about 5 microliters of the body fluid.

55. The kit of claim 51, wherein the slide further comprises at least one control chamber.

56. The kit of claim 51, wherein the slide and the imaging system are contained in a common housing.

57. The kit of claim 51, wherein the slide is removable.

58. The kit of claim 51, wherein the fluidic channel is across a surface of the slide.

59. The kit of claim 51, wherein the second reagent stains the white blood cell.

60. The kit of claim 51, wherein the body fluid is blood.

61. The kit of claim 51, wherein the body fluid is saliva.

62. The kit of claim 51, wherein the body fluid is urine.

63. The kit of claim 51, wherein the device has a mass of no greater than 2,000 g, wherein the device has a minimum total mass of about 100 g.

* * * * *